US012642766B2

(12) United States Patent
Chong et al.

(10) Patent No.: US 12,642,766 B2
(45) Date of Patent: Jun. 2, 2026

(54) EDB-FN AS BIOMARKER OF CANCER AND/OR BRAIN DISEASE AND NANODRUG DELIVERY SYSTEM TARGETING SAME

(71) Applicants: KOREA UNIVERSITY RESEARCH AND BUSINESS FOUNDATION, Seoul (KR); KOREA ADVANCED INSTITUTE OF SCIENCE AND TECHNOLOGY, Daejeon (KR)

(72) Inventors: Kyuha Chong, Seoul (KR); Phei Er Saw, Guangdong (CN); Jungsul Lee, Gyeonggi-do (KR)

(73) Assignees: KOREA UNIVERSITY RESEARCH AND BUSINESS FOUNDATION, Seoul (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 832 days.

(21) Appl. No.: 17/800,202

(22) PCT Filed: Feb. 17, 2021

(86) PCT No.: PCT/KR2021/002008
§ 371 (c)(1),
(2) Date: Aug. 16, 2022

(87) PCT Pub. No.: WO2021/167339
PCT Pub. Date: Aug. 26, 2021

(65) Prior Publication Data
US 2023/0109491 A1     Apr. 6, 2023

(30) Foreign Application Priority Data

Feb. 19, 2020   (KR) ........................ 10-2020-0020537
Feb. 9, 2021    (KR) ........................ 10-2021-0018153

(51) Int. Cl.
| | |
|---|---|
| *A61K 9/107* | (2006.01) |
| *A61K 47/62* | (2017.01) |
| *A61K 47/69* | (2017.01) |
| *A61K 49/08* | (2006.01) |
| *G01N 33/574* | (2006.01) |
| *G01N 33/575* | (2026.01) |
| *G01N 33/68* | (2006.01) |

(52) U.S. Cl.
CPC ............ *A61K 9/1075* (2013.01); *A61K 47/62* (2017.08); *A61K 47/6909* (2017.08); *A61K 49/08* (2013.01); *G01N 33/575* (2026.01); *G01N 33/68* (2013.01)

(58) Field of Classification Search
CPC .. A61K 9/1075; A61K 47/62; A61K 47/6909; A61K 49/08; G01N 33/574; G01N 33/68
See application file for complete search history.

(56) References Cited

FOREIGN PATENT DOCUMENTS

| | | |
|---|---|---|
| KR | 10-2015-0059444 | 6/2015 |
| KR | 10-1554564 | 9/2015 |
| KR | 10-2019-0099827 | 8/2019 |
| WO | 2009-006311 | 1/2009 |

OTHER PUBLICATIONS

P.E. Saw, et al. Aptide-conjugated liposome targeting tumor-associated fibronectin for glioma therapy, J. Mater. Chem. B, 2013, 4723-4726. (Year: 2013). Clted on ISA report.*
R. Wang, et al. Application of poly(ethylene glycol)-distearoylphosphatidylethanolamine (PEG-DSPE) block copolymers and their derivatives as nanomaterials in drug delivery. International Journal of Nanomedicine 2012: 7, 4185-4198. (Year: 2012).*
P.E. Saw, et al. "Effect of PEG Pairing on the Efficiency of Cancer-Targeting Liposomes," Theranostics 2015, vol. 5, Issue 7, 746-754. (Year: 2015).*
P.E. Saw, et al. "Effect of PEG Pairing on the Efficiency of Cancer-Targeting Liposomes," Theranostics 2015, vol. 5, Issue 7, 746-754, supplementary material. (Year: 2015).*
Karina Esparza, Dulari Jayawardena, and Hayat Onyuksel. "Phospholipid Micelles for Peptide Drug Delivery," Chapter 4 of Pharmaceutical Nanotechnology: Basic Protocols, Methods in Molecular Biology, Volkmar Weissig and Tamer Elbayoumi (eds.), vol. 2000, 2019, 43-57. (Year: 2019).*
B-J Zhao, et al. "The antiangiogenic efficacy of NGR-modified PEG-DSPE micelles containing paclitaxel (NGR-M-PTX) for the treatment of glioma in rats A1," Journal of Drug Targeting, 2011; 19(5): 382-390. (Year: 2011).*
Chong K, et al. Enhancement of the photocytotoxic efficiency of sub-12 nm herapeutic polymeric micelles with increased co-localisation in mitochondria. Chem Commun (Camb). 2013; 49: 11476-8.
Saw, P.E. et al. Aptide-conjugated liposome targeting tumor-associated fibronectin for glioma therapy. J. Mater. Chem. B. 2013, vol. 1, pp. 4723-4726.

(Continued)

Primary Examiner — Michael P Cohen
(74) Attorney, Agent, or Firm — Casimir Jones, S.C.; Robert A. Goetz

(57) ABSTRACT

The present invention relates to a drug delivery system with a micelle structure comprising a $PEG_{2000}$-DSPE polymerized lipid and an $APT_{EDB}$-$PEG_{2000}$-DSPE polymer, and a preparation method thereof. The drug delivery system targets extra-domain B of fibronectin (EDB-FN), which is overexpressed in a brain tumor, and can pass through the blood-brain barrier (BBB) or the blood-brain tumor barrier (BBTB) to deliver a drug specifically to the brain tumor cells. In addition, the present invention can provide a pharmaceutical composition for diagnosing or treating a brain tumor, comprising the drug-loaded drug delivery system as an active ingredient. The composition can be accumulated inside the brain tumor and incorporated into the tumor cells to specifically inhibit tumor growth, and thus can be efficiently utilized for diagnosing or treating a brain tumor.

8 Claims, 9 Drawing Sheets

Specification includes a Sequence Listing.

(56) References Cited

OTHER PUBLICATIONS

Yang, Q. et al. Cabozantinib Loaded DSPE-PEG2000 Micelles as Delivery System: Formulation, Characterization and Cytotoxicity Evaluation. BAOJ Pharm. Sci. Jan. 5, 2015, vol. 1, pp. 1-13.

Saw, P.E. et al. Effect of PEG Pairing on the Efficiency of Cancer-Targeting Liposomes. Theranostics. 2015, vol. 5, No. 7, pp. 746-754.

International Search Report, International Patent Application No. PCT/KR2021/002008, mailed Jun. 4, 2021, 5 pages.

Zhao Bo-Jun et al. "The antiangiogenic efficacy of NGR-modified PEG-DSPE micelles containing paclitaxel (Ngr-M- Ptx) for the treatment of glioma in rats", Journal of Drug Targeting, 2011; 19(5): 382-390.

Saw Phei Er et al. "Hyper-cell-permeable micelles as a drug delivery carrier for effective cancer therapy", Biomaterials 123 (2017) 118-126.

Saw Phei Er et al. "Extra-domain B of fibronectin as an alternative target for drug delivery and a cancer diagnostic and prognostic biomarker for malignant glioma", Theranostics 2021; 11(2): 941-957.

* cited by examiner

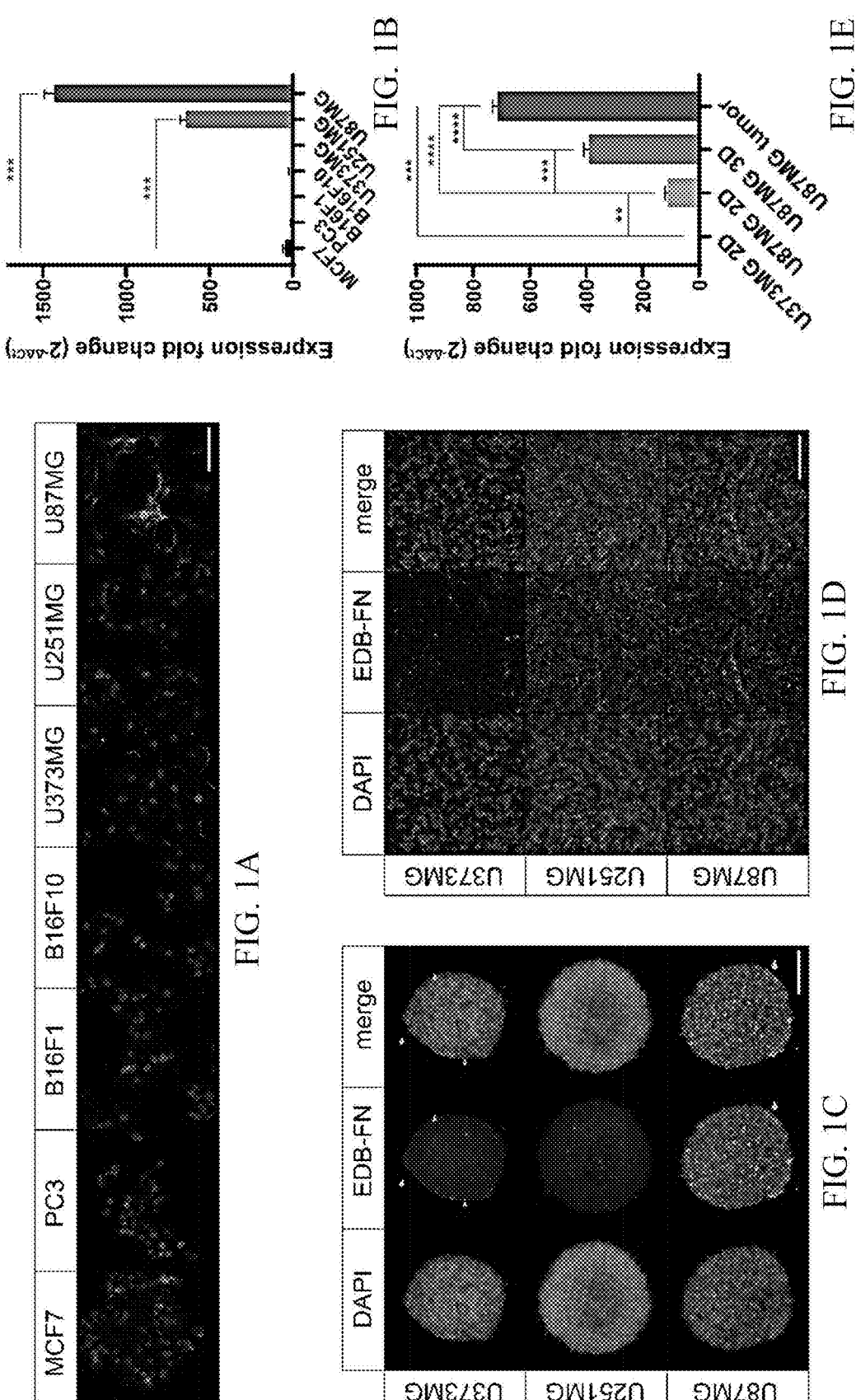

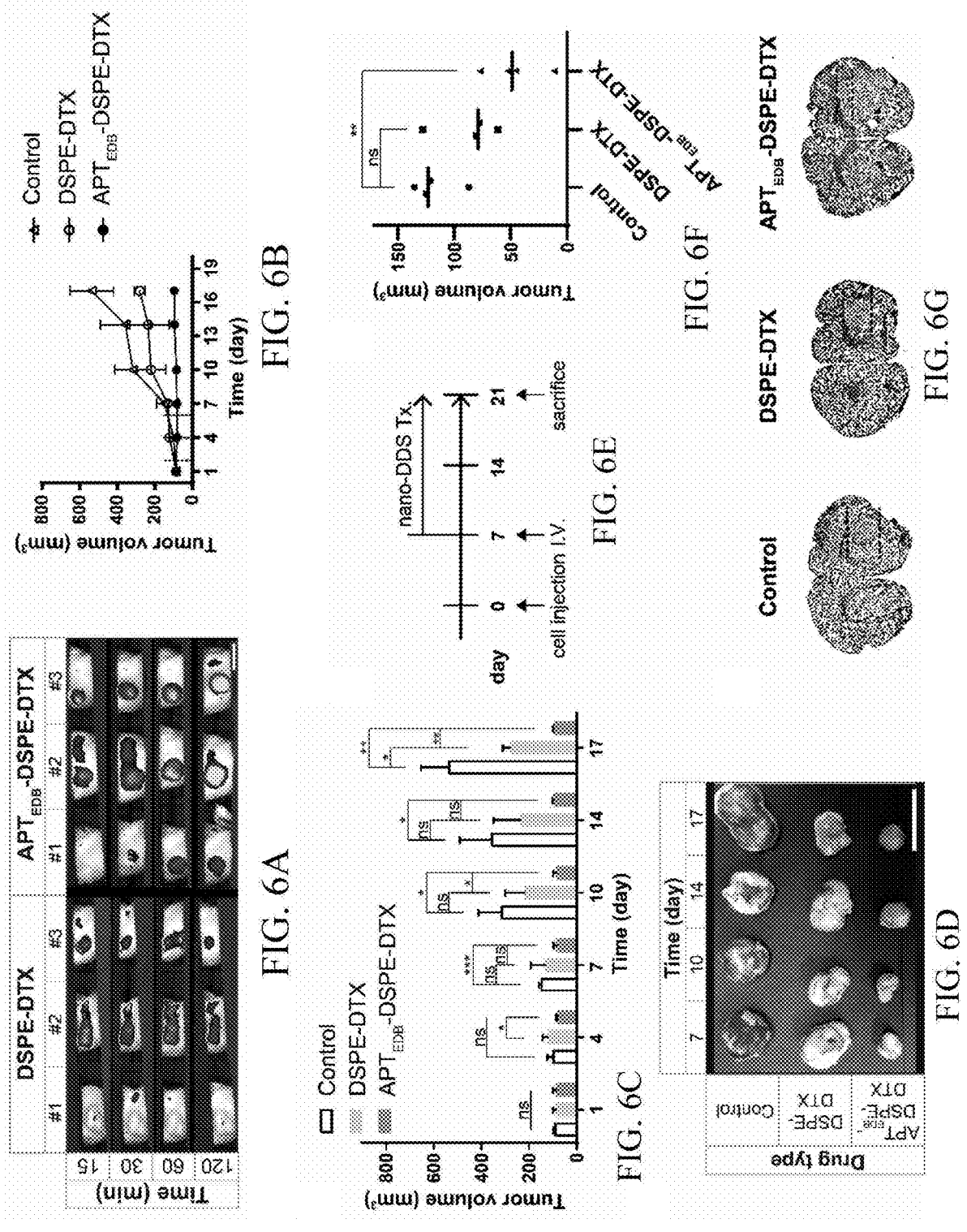

SEQUENCE LISTING

<160> NUMBER OF SEQ ID NOS: 1

<210> SEQ ID NO 1
<211> LENGTH: 25
<212> TYPE: PRT
<213> ORGANISM: Homo sapiens
<220> FEATURE:
<221> NAME/KEY: CHAIN
<222> LOCATION: (15)
<223> OTHER INFORMATION: K is attached by C

<400> SEQUENCE: 1

Cys Ser Ser Pro Ile Gln Gly Ser Trp Thr Trp Glu Asn Gly Lys Trp
1               5                   10                  15

Thr Trp Gly Ile Ile Arg Leu Glu Gln
            20                  25

EDB-FN AS BIOMARKER OF CANCER AND/OR BRAIN DISEASE AND NANODRUG DELIVERY SYSTEM TARGETING SAME

TECHNICAL FIELD

The following description relates to a nanodrug delivery system that targets extradomain B of fibronectin (EDB-FN) overexpressed in brain tumors, and the like.

BACKGROUND ART

Malignant glioma (MG) is one of the dreaded tumors that are difficult to cure even with aggressive treatment. Glioblastoma multiforme (GBM) is the most malignant and common glioma, with an average survival time of fewer than two years despite surgical and medical treatment. Malignant gliomas proliferate rapidly, have high invasiveness, and are difficult to treat due to cellular heterogeneity with the blood-brain barrier and the blood-brain tumor barrier (BBTB). To overcome the above limitations, molecular and genetic studies on the classification of brain tumors are more important. This has had an impact on applying molecular biology to pathological classification and improving diagnostic and therapeutic strategies.

Representative phenotype-genotype diagnostic markers currently used are as follows: $O^6$-methylguanine-deoxyribonucleic acid (DNA)methyltransferase promoter (MGMT) methylation, isocitrate dehydrogenase-1 (IDH-1) mutation, and chromosomal 1p/19q deletion. Evaluating the above markers has a great influence on prognosis prediction and suggesting treatment tailored to each patient. Further, many other biomarkers such as alpha-thalassemia/mental retardation syndrome X-linked and telomerase reverse transcriptase promoter mutations are still being validated, and their effectiveness is being actively demonstrated. However, so far, most of the biomarkers have not been evaluated and proven in malignant gliomas, and thus they do not develop into therapeutic agents. Therefore, there is still a need to devise biomarkers that can be used for effective diagnosis and treatment.

Fibronectin is a glycoprotein mainly found in the extracellular matrix and plasma membrane. It regulates cell migration and adhesion while binding to various extracellular matrix proteins such as integrins, collagen, and fibrin. The fibronectin monomers are classified into three types (types I, II, and III) according to their repeating units. The alternative splicing domains prepared in the three regions of the fibronectin gene have a constant splicing pattern. The resulting isoforms are named according to the splicing site located in type III repeating unit: extra-domain A (EDA-FN), Extra-domain B (EDB-FN), and type III connecting segment (IIICS-FN). EDB-FN is an oncofetal antigen. EDB-FN is overexpressed in a variety of human cancers, such as non-small cell lung carcinoma, Hodgkin lymphoma, and prostate cancer. In addition, EDB-FN is utilized as an angiogenesis marker for head and neck cancer. Despite the role of fibronectin in the brain, EDB-FN can be utilized as a tracking tool for diagnosing major glioblastoma multiforme in patients and proposed as a new target for the treatment of glioblastoma multiforme and the radioimmunotherapy of glioma in rodent models. Despite the active research on EDB-FN, the role of EDB-FN is still unknown.

Previously, studies comparing EDB-FN expression levels in cancers of all major organs have not been conducted, and studies including prognosis prediction through EDB-FN expression using bioinformatics datasets have not yet been performed.

Previously, a study was performed on a nanodrug delivery system of inorganic superparamagnetic iron oxide nanoparticles (SPIONs) with a specific size of 34 nm targeting EDB-FN or a drug delivery system of a liposome structure with a size of 115±13 nm. However, in the case of a nanodrug delivery system with a size of 12 nm or more, there have been reports of limitations in drug delivery from preclinical studies due to the limitations of the cerebrovascular barrier and the cerebrovascular tumor barrier. Therefore, the present inventors completed the present invention by studying EDB-FN as a potential diagnostic biomarker for malignant glioma and developing a micelle-structured nanodrug delivery system with a size of 12 nm or less to target it.

DISCLOSURE OF THE INVENTION

Technical Goals

An aspect provides a micelle-structured drug delivery system including a $PEG_{2000}$-DSPE polymerized lipid and an $APT_{EDB}$-$PEG_{2000}$-DSPE polymer, in which the $APT_{EDB}$ is an aptide showing a specific binding ability to extradomain B of fibronectin (EDB-FN) gene (FN1, Entrez Gene ID: 2335).

Another aspect provides a pharmaceutical composition for diagnosing or treating brain tumors including the drug-loaded drug delivery system as an active ingredient.

Still another aspect provides a method for preparing a brain tumor-specific drug delivery system including the following steps of:

(1) mixing $APT_{EDB}$ containing cysteine residues and Mal-$PEG_{2000}$-DSPE in an organic solvent in a molar ratio of 1:2 and inducing polymerization;

(2) obtaining an $APT_{EDB}$-$PEG_{2000}$-DSPE polymer from the mixed solution of step (1);

(3) mixing the $APT_{EDB}$-$PEG_{2000}$-DSPE polymer and $PEG_{2000}$-DSPE polymerized lipid in one or more solvents selected from the group consisting of water, PBS, HBS, and HBG to induce the formation of a micelle structure; and (4) filtering the mixed solution of step (3) and purifying the micellar structure.

Yet another aspect provides a method of producing a drug for treating brain tumors, the method including steps (1) to (4) as described above, in which the step (3) is performed in which an anti-cancer agent is additionally mixed in a solution in which the $APT_{EDB}$-$PEG_{2000}$-DSPE polymer and $PEG_{2000}$-DSPE polymerized lipid are dissolved, thereby inducing the formation of a micelle structure.

However, the technical problem to be achieved by the present invention is not limited to the above-mentioned problems, and other problems not mentioned will be clearly understood by those skilled in the art from the following description.

Technical Solutions

According to an aspect, there is provided a micelle-structured drug delivery system including a $PEG_{2000}$-DSPE polymerized lipid and an $APT_{EDB}$-$PEG_{2000}$-DSPE polymer.

As an example embodiment of the present invention, the $APT_{EDB}$ is an aptide that shows the specific binding ability to extradomain B of fibronectin (EDB-FN) gene (Entrez Gene ID: 2335).

As another example embodiment of the present invention, the drug delivery system may include 1 to 2.5 parts by weight of the $APT_{EDB}$-$PEG_{2000}$-DSPE polymer based on 100 parts by weight of the $PEG_{2000}$-DSPE polymerized lipid.

As another example embodiment of the present invention, the diameter of the drug delivery system may be 5.0 to 12.0 nm, and the zeta potential of the drug delivery system may be −8.0 to −11.0.

As another example embodiment of the present invention, the drug delivery system may pass through the blood-brain barrier (BBB) or blood-brain tumor barrier (BBTB) to deliver the drug specifically to brain tumor cells.

According to another aspect, there is provided a pharmaceutical composition for diagnosing or treating brain tumors including the drug-loaded drug delivery system as an active ingredient.

According to another aspect, there is provided a method for preventing or treating brain tumors including administering the drug-loaded drug delivery system to an individual.

According to another aspect, there is provided the use of the drug-loaded drug delivery system for the preparation of a drug for the prevention or treatment of brain tumors.

According to another aspect, there is provided a method for diagnosing a brain tumor including administering the drug-loaded drug delivery system to an individual.

According to another aspect, there is provided the use of the drug-loaded drug delivery system for the preparation of a drug for the diagnosis of brain tumors.

As an example embodiment of the present invention, the drug may be a contrast agent or an anti-cancer agent, and the anti-cancer agent may include any one or more selected from the group consisting of docetaxel, halaven, vincristine, cisplatin, vinblastine, vinorelbine, paclitaxel, etoposide, topotecan, irinotecan, dactinomycin, doxorubicin, daunorubicin, mitomycin, gleevec, carboplatin, valrubicin, flutamide, gemcitabine, bleomycin, temozolomide, procarbazine, lomustine (CCNU; 1-(2-chloroethyl)-3-cyclohexyl-1-nitrosourea), vincristine, and carmustine (BCNU).

As another example embodiment of the present invention, there is provided the brain tumor may include any one or more selected from the group consisting of astrocytoma, glioblastoma multiforme, oligodendroglioma, oligoastrocytoma, ependymoma, medulloblastoma, hemangioblastoma, meningioma, pituitary adenoma, craniopharyngioma, and choroid plexus papilloma.

According to another aspect, there is provided a method of producing a brain tumor-specific drug delivery system, the method including steps of:
   (1) mixing $APT_{EDB}$ containing cysteine residues and Mal-$PEG_{2000}$-DSPE in an organic solvent in a molar ratio of 1:2 and inducing polymerization;
   (2) obtaining an $APT_{EDB}$-$PEG_{2000}$-DSPE polymer from the mixed solution of step (1);
   (3) mixing the $APT_{EDB}$-$PEG_{2000}$-DSPE polymer and $PEG_{2000}$-DSPE polymerized lipid in one or more solvents selected from the group consisting of water, PBS, HBS, and HBG to induce the formation of a micelle structure; and
   (4) filtering the mixed solution of step (3) and purifying the micellar structure.

As an example embodiment of the present invention, the organic solvent of step (1) may include at least one selected from the group consisting of chloroform, dimethyl sulfoxide, dimethylformamide, ethanol, methanol, tetrahydrofuran, toluene, xylene, and hexane.

As another example embodiment of the present invention, step (1) may be performed under inactive conditions for 12 hours at room temperature.

As another example embodiment of the present invention, step (2) may be performed to obtain an $APT_{EDB}$-$PEG_{2000}$-DSPE polymer from the mixed solution using liquid chromatography.

As another example embodiment of the present invention, step (3) may be performed in which $APT_{EDB}$-$PEG_{2000}$-DSPE polymer and $PEG_{2000}$-DSPE polymerized lipid are mixed in a solvent and sonicated to hydrate, thereby inducing the formation of a micelle structure.

As another example embodiment of the present invention, step (4) may be performed in which the mixed solution may be filtered with a 0.0025 to 0.1 μm membrane, and the micelle structure may be purified through size exclusion chromatography. The membrane may preferably be a 0.1 μm membrane.

According to another aspect, there is provided a brain tumor-specific drug delivery system prepared by the method, in which the drug delivery system has a diameter of 5.0 to 12.0 nm, and the zeta potential of the micelle structure is −8.0 to −11.0.

According to another aspect, there is provided a method of producing a drug for treating brain tumors, the method including steps (1) to (4) as described above, in which the step (3) is performed in which an anti-cancer agent is additionally mixed in a solution in which the $APT_{EDB}$-$PEG_{2000}$-DSPE polymer and $PEG_{2000}$-DSPE polymerized lipid are dissolved, thereby inducing the formation of a micelle structure.

As an example embodiment of the present invention, the anti-cancer agent may be mixed so that the final concentration is 50 mg/mL.

As another example embodiment of the present invention, the drug may pass through the blood-brain barrier (BBB) or blood-brain tumor barrier (BBTB) to be accumulated inside the brain tumor and incorporated into the tumor cells.

Advantageous Effects

The present invention relates to a drug delivery system having a micelle structure including a $PEG_{2000}$-DSPE polymerized lipid and an $APT_{EDB}$-$PEG_{2000}$-DSPE polymer, and a method for preparing the same. The drug delivery system targets extradomain B of fibronectin (EDB-FN), which is overexpressed in brain tumors, and may passe through the blood-brain barrier (BBB) or the blood-brain tumor barrier (BBTB) and deliver drugs specifically to brain tumor cells. In addition, the present invention may provide a pharmaceutical composition for diagnosing or treating brain tumors including the drug-loaded drug delivery system as an active ingredient, and the composition may be accumulated inside a brain tumor and be incorporated into tumor cells to specifically inhibit tumor growth, so it can be usefully used for diagnosis or treatment of brain tumors.

BRIEF DESCRIPTION OF DRAWINGS

FIG. 1 is a diagram illustrating the overexpression of EDB-FN in malignant glioma cells in order to demonstrate the expression of EDB-FN. FIG. 1A shows the EDB-FN expression pattern in a 2D culture of various cancer cell lines (size bar=100 μm). Green indicates EDB-FN; Blue indicates 4',6-diamidino-2-phenylindole (DAPI). FIG. 1B shows the results of EDB-FN mRNA expression analysis using quantitative real-time PCR (qRT-PCR) after extracting total RNA from 2D cultured cells of various cancers. $2^{-\Delta\Delta_{CT}}$ was used and glyceraldehyde 3-phosphate dehydrogenase was set as an internal control. The EDB-FN expression pattern was confirmed by immunofluorescence staining in 3D culture (size bar=200 μm). FIG. 1C shows the subcutaneously transplanted cancer tissue (size bar=100 μm). FIG. 1D shows a malignant glioma cell line. FIG. 1E is the result of performing qRT-PCR analysis using total RNA extracted from U373MG cells (2D monolayer culture) or U87MG cells (2D monolayer culture, 3D spheroid culture, and subcutaneous tumor tissue). Statistical analysis: Welch's t test. p<0.01, *p<0.001, ****p<0.0001, ns: not statistically significant. The results are expressed as mean±standard deviation of quadruplet determinations. EDB-FN: fibronectin extradomain B; MG: Malignant glioma.

FIG. 2 shows a result of analyzing the characterization of the synthetic $APT_{EDB}$-DSPE micellar nano-DDS.

FIG. 4 shows the in vitro EDB-FN- and time-dependent cellular uptake of $APT_{EDB}$-DSPE micellar nano-DDS.

FIG. 5 shows the in vitro cellular uptake and cytotoxicity of $APT_{EDB}$-DSPE and $APT_{EDB}$-DSPE-DTX micellar nano- DDS.

FIG. 6 shows the in vivo uptake and anti-cancer efficacy of $APT_{EDB}$-DSPE-DTX in the U87MG subcutaneous xenograft mouse model. FIG. 6A shows IVIS rhodamine B real-time images of PEG$_{2000}$-DSPE micellar nano-DDS and $APT_{EDB}$-DSPE micellar nano-DDS uptake in a U87MG xenograft tumor-bearing rodent model (n=3 mice per group). Size bar=10 mm. FIG. 6B shows the U87MG xenograft tumor growth curve according to drug treatment. Tumor size in mice was measured every three days (n=4 mice per group). The red arrow indicates the drug IV infusion schedule. FIG. 6C shows the anti-cancer effect of micellar nano-DDS. Tumor size changes were shown according to DSPE-DTX, $APT_{EDB}$-DSPE-DTX, or saline treatment, and saline was used as a negative control group for the comparison (n=4 mice per group). FIG. 6D shows a representative image of a tumor excised from a xenograft model. Drug-treated mice were sacrificed on days 7, 10, 14, and 17, respectively (n=1 mouse per group). Size bar=10 mm. In the U87MG subcutaneous xenograft mouse model, FIG. 6E shows the experimental schedule of the orthotopic model, and FIG. 6F shows the inhibitory effect of micellar nano-DDS on malignant brain tumors (n=4 per group). Brain slices with the largest tumor volume were selected and analyzed in each sample. FIG. 6G is a representative image showing the comparison of brain tumor sizes. Mouse brains were cut to a thickness of 20 μm, and brain tumors were indicated by H&E staining. Size bar=1 mm. Statistical analysis: Welch's t test. *p<0.05, p<0.01, *p<0.001, ****p<0.0001, ns: not statistically significant. The results are expressed as mean±standard deviation. $APT_{EDB}$-DSPE-DTX: docetaxel-loaded $APT_{EDB}$-DSPE micellar nano-DDS; DDS: drug delivery system; DSPE-DTX: docetaxel-loaded PEG$_{2000}$-DSPE micellar nano-DDS; DTX: docetaxel; nano DDS Tx: nano drug delivery system treatment.

FIG. 7 shows the in vivo biocompatibility of $APT_{EDB}$-DSPE-DTX.

7B shows the minimal toxicity of micellar nano-DDS to normal major organs. At the end of the experiment (day 17, when the tumor volume was 80 to 120 mm$^3$), the heart, liver, spleen, lung, and kidney were extracted from the U87MG flank xenograft model, and H&E staining was performed. Size bar=100 μm.

FIG. 8 shows EDB-FN expression in an orthotopic xenograft model. More specifically, the expression of EDB-FN is shown in orthotopic xenografted brain tumors. The model mice were injected with saline (control), DSPE-DTX, or APT$_{EDB}$-DSPE-DTX micellar nano-DDS for two weeks. The mouse brain was dissected to a thickness of 20 μm.

BEST MODE FOR CARRYING OUT THE INVENTION

As a result of intensive research on extradomain B of fibronectin (EDB-FN) overexpressed in brain tumors, the present inventors developed a nanodrug delivery system targeting EDB-FN to complete the present invention.

More specifically, it was confirmed that the APT$_{EDB}$-DSPE micellar nano agent containing APT$_{EDB}$: PEG$_{2000}$-DSPE=1:2 has a higher EDB-FN affinity than the micellar nano agent formed from the polymerized lipid PEG$_{2000}$-DSPE, and thus the cell uptake rate in brain tumors is higher, it can accumulate a lot in the tumor, the nano agent can easily penetrate the blood-brain tumor barrier as 12 nm or less, the nano drug delivery system containing the nano agent has a high tumor inhibitory effect, and the anti-cancer efficacy is high because it does not affect normal tissues and other organs.

In the present invention, the term "aptide" refers to an aptamer-like peptide with improved stability while maintaining affinity for a target. The aptide has a scaffold composed of a cyclic β-hairpin-based peptide binder and n amino acids at both ends of the scaffold, which can bind to a specific biological target. Aptide may include a target-binding region capable of constructing various libraries. The aptide may be composed of any one or more amino acids selected from the group consisting of L-amino acids and D-amino acids. The term "stability" may include the physical, chemical, and biological stability of aptide, and specifically may refer to biological stability. That is, the biologically stable aptide may have resistance to the action of proteolytic enzymes in vivo.

Figures 2A, 2B, 2C:
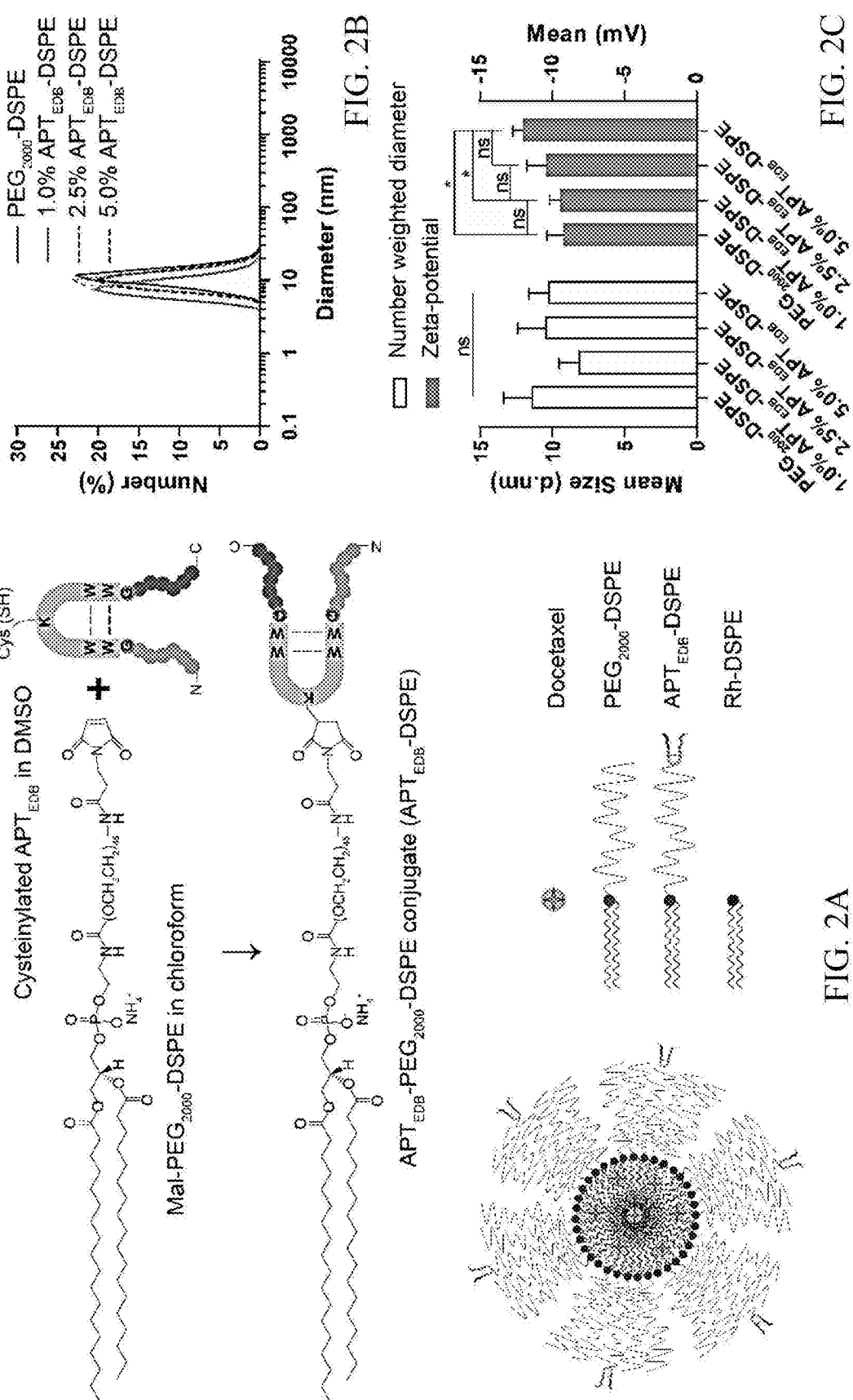
FIG. 2A shows a synthetic method using Mal-PEG$_{2000}$-DSPE and cysteinylated $APT_{EDB}$ and a representative formulation of $APT_{EDB}$-DSPE micellar nano-DDS ($APT_{EDB}$-DSPE-DTX) encapsulated with docetaxel.
FIG. 2B shows the dynamic light scattering (DLS) size measurements of PEG$_{2000}$-DSPE micellar nano-DDS ($APT_{EDB}$-unconjugated) and $APT_{EDB}$-DSPE micellar nano-DDSs ($APT_{EDB}$-conjugated), and both nanoparticles were smaller than 12 nm. (3 replicates per group).
FIG. 2C shows that all nanoparticle formulations have negative zeta potential. As the $APT_{EDB}$-DSPE concentration increases, the zeta potential of nano-DDS becomes more negative. Statistical analysis: Welch's t test. *p<0.05, ns: not statistically significant. The results are expressed as mean±standard deviation of quadruplet determinations. DMSO: dimethyl sulfoxide; PEG$_{2000}$-DSPE: polyethylene glycol $_{(2000)}$-1,2-distearoyl-sn-glycero-3-phosphoethanolamine (ammonium salt); Rh-DSPE: DSPE-N-(lissamine rhodamine B sulfonyl) (ammonium salt).

The aptide according to the present invention is an aptide that specifically binds to the EDB-FN gene (Entrez Gene ID: 2335) and may be specifically composed of the amino acid sequence represented by SEQ ID NO: 1. The amino acid sequence may be characterized in that a cysteine (C) residue is attached to a lysine (K) (FIG. 2A). The aptide for EDB-FN is stable with a size of 3 kDa, and can bind to EDB-FN with a high affinity of <100 nM.

TABLE 1

| APT$_{EDB}$ amino acid sequence | N'-CSSPIQGSWTWENGK(C)-WTWGIIRLEQ-C' | SEQ ID NO: 1 |
|---|---|---|

The aptide may be a variant or fragment of the aptide having a different sequence by deletion, insertion, substitution, or a combination of amino acid residues within a range that does not affect the structure and activity of the aptide according to the present invention Amino acid exchanges in proteins or peptides that do not entirely alter the activity of the molecule are known in the art. In some cases, it may be modified by phosphorylation, sulfation, acrylation, saccharification, methylation, farnesylation, and the like. The aptide may have 70, 80, 85, 90, 95, or 98% homology to the amino acid sequence represented by SEQ ID NO: 1.

In the present invention, the term "drug delivery system" refers to a composite chemically or physically bound to an active ingredient (e.g., drug) to a target cell, tissue, or organ and means a carrier or vehicle suitable for transporting and delivering the active ingredient. The chemical bond refers to a chemical bond through a chemical reaction, and the physical bond is a concept that includes not only physical fixation such as adsorption, cohesion, entanglement, and entrapment but also non-chemical fixation in which an electrical interaction such as van der Waals bonds occurs either alone or in conjunction with the physical fixation.

In the present invention, the term "nano drug delivery system" means that the drug delivery system has a size range of about 1 nanometer (nm) to about 1000 nm. The nano drug delivery system may be a pharmaceutically acceptable carrier.

The term "drug" has pharmacological activity and includes polypeptides, proteins, and the like, and in the present invention, preferably means a contrast agent or an anti-cancer agent. Specific examples of the anti-cancer agent include docetaxel, halaven, vincristine, cisplatin, vinblastine, vinorelbine, paclitaxel, etoposide, topotecan, irinotecan, dactinomycin, doxorubicin, daunorubicin, mitomycin, gleevec, carboplatin, valrubicin, flutamide, gemcitabine, bleomycin, temozolomide, procarbazine, lomustine (CCNU; 1-(2-chloroethyl)-3-cyclohexyl-1-nitrosourea), vincristine, or carmustine (BCNU), and the like, but are not limited thereto.

In the present invention, the term "prevention" refers to any action that inhibits or delays the occurrence, spread, or recurrence of cancer by administration of the composition of the present invention, and "treatment" refers to any action that improves or advantageously changes the symptoms of the disease by administration of the composition of the present invention.

In the present invention, "diagnosis" includes determining the susceptibility of an individual to a specific disease or disorder, determining whether an individual currently has a specific disease or disorder, determining the prognosis of an individual suffering from a specific disease or disorder, or therametrics (e.g., monitoring an individual's condition to provide information about treatment efficacy).

In the present invention, the term "pharmaceutical composition" means one prepared for the purpose of preventing or treating a disease, and each may be formulated and used in various forms according to a conventional method. For example, it may be formulated in oral dosage forms such as powders, granules, tablets, capsules, suspensions, emulsions, and syrups, and may be formulated and used in the form of external preparations, suppositories, and sterile injection solutions.

In the present invention, "included as an active ingredient" means that the ingredient is included in an amount necessary or sufficient to realize a desired biological effect. In actual application, the amount included as an active ingredient is an amount for treating the target disease and may be determined in consideration of matters that do not cause other toxicity. It can vary depending on various factors such as, for example, the disease or condition being treated, the type of composition being administered, the size of the subject, or the severity of the disease or condition. A person of ordinary skill in the art to which the present invention pertains can empirically determine the effective amount of an individual composition without undue experimentation.

The composition of the present invention may be administered orally or parenterally in a pharmaceutically effective amount according to the desired method, and the term "pharmaceutically effective amount" of the present invention refers to an amount sufficient to treat a disease at a reasonable benefit/risk ratio applicable to medical treatment and not to cause side effects, and the effective dose level may be determined according to factors including the patient's health condition, severity, drug activity, sensitivity to a drug, administration method, administration time, administration route, excretion rate, duration of treatment, combined or concurrent drugs, and other factors well known in the medical field.

Therefore, the pharmaceutical composition of the present invention may be administered to an individual to prevent, treat, and/or diagnose brain tumors, and the "brain tumor" refers to all pre-cancerous and cancerous cells that exhibit all new cell growth and proliferation, whether malignant or benign and preferably means malignant glioma. Non-limiting examples include astrocytoma, glioblastoma multiforme, oligodendroglioma, oligoastrocytoma, ependymoma, medulloblastoma, hemangioblastoma, meningioma, pituitary adenoma, craniopharyngioma, or choroid plexus papilloma.

In the present invention, the term "individual" may be a mammal, such as a rat, livestock, mouse, or human, preferably a human.

The pharmaceutical composition of the present invention may be formulated in various forms for administration to an individual, and a representative formulation for parenteral administration is an injection formulation, preferably an isotonic aqueous solution or suspension. An injection formulation may be prepared according to techniques known in the art using suitable dispersing or wetting agents and suspending agents. For example, each ingredient may be prepared into a dosage form for injection by dissolving in saline solution or buffer solution. Further, the formulation for oral administration includes, for example, ingestible tablets, buccal tablets, troches, capsules, elixirs, suspensions, syrups, wafers, and/or the like. These formulations may include, in addition to the active ingredient, diluents (e.g., lactose, dextrose, sucrose, mannitol, sorbitol, cellulose, and/or glycine) and lubricants (e.g., silica, talc, stearate, and magnesium or calcium salt thereof, and/or polyethylene glycol). The tablets may include a binder such as magnesium aluminum silicate, starch paste, gelatin, tragacanth, methylcellulose, sodium carboxymethylcellulose, and/or polyvinyl pyrrolidine, and depending on needs, may additionally include disintegrating agents such as starch, agar, alginic acid, or sodium salt, absorbents, colorants, flavoring agents, and/or sweetening agents. The formulation may be prepared by general mixing, granulating, or coating methods.

Further, the pharmaceutical composition according to the present invention may additionally include adjuvants such as preservatives, wettable powders, emulsion activators, salt for osmotic regulation, or buffer, and other therapeutically useful materials and may be formulated by known methods.

The pharmaceutical composition according to the present invention may be administered through several routes including oral, transdermal, subcutaneous, intravenous, or intramuscular administration, and the dosage of the active ingredient may be appropriately selected depending on several factors such as the route of administration, age, sex, weight, and severity of the patient. In addition, the composition of the present invention may be administered in combination with a known compound capable of enhancing the desired effect.

In the present invention, the term "animal model" refers to an animal having a disease that is very similar to a human disease. The significance of disease model animals in the study of human diseases is due to the physiological or genetic similarity between humans and animals. For disease research, biomedical disease model animals provide research materials for various causes, pathogenesis, and diagnosis of diseases. The study of disease model animals allows us to find out genes related to diseases and to understand the interactions between genes. Further, it is possible to obtain basic data for determining the feasibility of practical use through actual efficacy and toxicity tests of the developed new drug candidates. The term "animal" or "experimental animal" refers to any mammalian animal other than humans. Such animals include animals of all ages, including embryos, fetuses, newborns, and adults. Animals for use in the present invention are, for example, commercially available. Such animals include laboratory animals or other animals, rabbits, rodents (e.g., mice, rats, hamsters, gerbils, and guinea pigs), cattle, sheep, pigs, goats, horses, dogs, cats, birds (e.g., chickens, turkeys, ducks, and geese), and primates (e.g., chimpanzees, monkeys, and rhesus monkeys) but are not limited thereto.

In the present invention, the term "culture" refers to growing an organism or a part of an organism (organs, tissues, cells, etc.) under appropriately artificially controlled environmental conditions. In this case, as external conditions, temperature, humidity, light, gaseous composition (partial pressure of carbon dioxide or oxygen), etc., are important. In addition, the most important direct influence on the cultured organism is the medium (incubator), which is the direct environment of the organism and a supply site for various nutrients necessary for survival or proliferation.

In the present invention, the term "in vitro culture" refers to a series of laboratory processes in which cells and the like are cultured in a laboratory incubator under conditions similar to the internal body environment in a manner which is distinct from the growing state in the body.

In the present invention, the term "medium" or "medium composition" refers to a mixture for the growth and proliferation of cells in vitro, including essential elements for the growth and proliferation of cells, such as sugar, amino acids, various nutrients, serum, growth factors, and minerals.

Best Mode for Carrying Out the Invention

Since the present invention may include various modifications and may have various example embodiments, the following specific example embodiments will be illustrated in the drawings and described in detail in the detailed description. However, it should be understood that this is not intended to limit the present invention to specific example embodiments, and all modifications, equivalents, and substitutes are included in the spirit and scope of the present invention. In describing the present invention, if it is determined that a detailed description of a related known technology may obscure the gist of the present invention, the detailed description thereof will be omitted.

<Example 1> Gene Expression Profile and Survival Analysis

All gene expression profiles were downloaded from Oncopression, and EDB-FN-related data were collected by studying fibronectin 1 (FN1, Entrez Gene ID: 2335), also known as FN or ED-B. Variants of the FN1 gene were investigated using ClinVar (https://www.ncbi.nlm nih.gov/clinvar), and 126 variants were identified. Because a transcriptomics database analysis was performed in order to screen for expression levels in malignant gliomas, analysis of variants was not performed in the present invention. The transcriptomics expression level of EDB-FN was normalized with Single Channel Array Normalization and Universal exPression Codes (SCAN.UPC) package of R, and expressed as UPC values. More specifically, a single sample normalization method was used for oncopression data, and all samples were obtained from the Affymetrix Human Genome U133 Plus 2.0 (GPL570 or A-AFFY-44) platform. Expression values ranged from 0.0 to 1.0, with 1.0 indicating complete transcriptional activation. The ratio of cancer cells to normal cells (cancer-to-normal ratio) was calculated by dividing the expression value in cancer cells by the average expression value in normal cells. For survival analysis, after collecting brain tumor datasets, including expression profiles and patient prognostic information, up to 30 samples were excluded from the analysis. All gene expression values were quantile normalized by the dataset. Z-value was calculated by log-rank test with each dataset, and averaged by the Liptak method using the square root of the number of patients in each dataset as body weight.

<Example 2> Sample Preparation and Interpretation of Patient Tissue Microarray (TMA)

Patient tissue samples were stored in paraffin blocks after surgery and pathological diagnosis, and the patients were 21 adults, aged 18 to 75 years, and were diagnosed with glioblastoma multiforme. Tissue microarray slides were prepared to contain a total of 65 tissue samples from 3 to 4 different tumor sites for each patient. The tissue core with a diameter of 2 mm was implanted with a recipient paraffin block containing 45 holes for each block. The blocks filled with paraffin were cut into 3 μm thick and placed on slides. Then, the tissue was stained as described in the immunohistochemistry section to be described later. After immunostaining, a readout was obtained for the presence and level of EDG-FN via blind review from a pathologist. The staining intensity ranged from none or '1+' (very weak positivity) to '4+' (very strong positivity). In the present invention, '1+' and '2+' were classified as a low-expression group, and '3+' and '4+' were classified as a high-expression group. In order to analyze the correlation between EDB-FN expression and prognostic prediction of a patient, a task of correlating the results of EDB-FN expression levels with the clinical data of each patient in patient tissue microarrays was performed.

The patient prognosis was analyzed using progression-free survival (PFS) and overall survival (OS) as variables.

Example <3> Materials

Polyethylene glycol $(_{2000})$-1,2-distearoyl-sn-glycero-3-phosphoethanolamine (ammonium salt) ($PEG_{2000}$-DSPE), DSPE-N-(lissamine rhodamine B sulfonyl) (ammonium salt) (Rh-DSPE), and N-maleimide-$PEG_{2000}$-DSPE (ammonium salt) (Mal-$PEG_{2000}$-DSPE) were purchased from Avanti Polar Lipids (CA, USA). The EDB-FN-specific peptide N'-CSSPIQGSWTWENGK(C)WTWGIIRLEQ-C' was custom-made by Anygen Corp (Gwangju, Republic of Korea). Mouse anti-EDB-FN antibody and anti-mouse fluorescein isothiocyanate (FITC)-conjugated secondary antibody were purchased from Abcam (Cambridge, UK). Docetaxel (DTX) and Sepharose CL-4B columns were purchased from Sigma-Aldrich (MO, USA). Mounting solution was purchased from Dako Diagnostics (Glostrup, Denmark). An Alamar Blue assay kit was purchased from Thermo Fisher Scientific (MA, USA). All reagents were laboratory grade and used as received.

<Example 4> Cell Culture

U87MG, U251MG, U373MG, MCF-7, PC3, B16F10, and B16F1 cells were purchased from American Type Culture Collection (VA, USA). All cells were maintained at 37° C. in a humidified 5% $CO_2$ environment. Cells were supplemented with 10% fetal bovine serum (FBS; Gibco, IL, USA), 100 U/mL penicillin (Gibco), and 100 μg/mL streptomycin (Gibco) and cultured in minimal essential medium (MCF-7), RPMI (PC3, B16F10, B16F1), or Dulbecco's modified Eagle's medium (U87MG, U251MG, U373MG). All of the above cell culture media were purchased from Gibco.

<Example 5> In Vitro 3D Spheroid Culture

For 3D spheroid culture, all three malignant glioma cell lines (U87MG, U251MG, and U373MG) were cultured at 1 to $5×10^3$ cells per well in a Nunclon Sphera Microplate 96-well round bottom plate (Thermo Fisher Scientific). The plate was centrifuged at 200×g for 2 min and then placed in a 37° C., 5% $CO_2$ incubator. The cells were cultured for six days, and half of the medium was changed on the 3rd day. For imaging, the formed spheroids were transferred to an 8-well chambered coverglass slide (Thermo Fisher Scientific) fixed with 4% (w/v) paraformaldehyde (Wako, VA, USA), followed by immunocytochemistry to be described later.

<Example 6> Malignant Glioma (MG) Flank Xenograft Model for In Vivo EDB-FN Immunocytochemistry In order to form a flank subcutaneous xenograft mouse model (n=1 mouse per group), U87MG, U251MG, and U373MG cells were injected into the right flank of BALB/c nude mice at $5×10^6$ cells per mouse. When the tumor volume reached 80 to 120 $mm^3$, mice were sacrificed, and immunocytochemistry of the excised tumor was performed.

<Example 7> Real-Time Quantitative Reverse Transcription-Polymerase Chain Reaction Cells were collected, and ribonucleic acid (RNA) was extracted with RiboEx using an RNA isolation kit (GeneAll, Seoul, Republic of Korea). Complementary DNA (cDNA) was synthesized by reverse transcription using a total of 1 µg of RNA from each sample. As a result, the following genes were estimated: EDB-FN gene (forward primer: 5'-AACT-CACTGACCTAAGCTTT-3'; reverse primer: 5'-CGTTTGTTGTGTCAGTGTAG-3'); glyceraldehyde 3-phosphate dehydrogenase) gene (forward primer: 5'-AATCCCATCACCATCTTCCA-3'; reverse primer: 5'-TGGACTCCACGACGTACTCA-3'. The polymerase chain reaction protocol was as follows: initial denaturation at 94° C. for 5 min; 30 repetitions of denaturation at 94° C. for 1 min, primer annealing at 55° C. for 1 min, and extension at 72° C. for 2 min; and final extension at 72° C. for 7 min 1 µg of cDNA was added to 4 µL of ultrapure water, 5 µL of SYBR Green real-time mixture (Takara, Tokyo, Japan) was added before performing a real-time polymerase chain reaction (Qiagen, Tokyo, Japan). The messenger RNA (mRNA) level of each gene was quantified using the $2^{-\Delta\Delta Ct}$ method and normalized with the messenger RNA of glyceraldehyde 3-phosphate dehydrogenase.

<Example 8> Cell and Tissue Staining 8.1. Immunocytochemistry

For 2D staining of seven different cell lines, 10,000 cells were cultured on 8-well chambered cover glass slides for 24 hours before staining. For 3D staining, spheroids were transferred from cultured dishes to 8-well chambered cover glass slides. The cultured cells were washed three times with cold phosphate buffered saline (PBS; Welgene, Gyeongsan, Republic of Korea), fixed with 4% (w/v) paraformaldehyde for 15 minutes at room temperature, washed with PBS, permeabilized with 0.1% (v/v) Triton X-100 (Amresco, PA, USA)/PBS for 10 min, and cultured with primary antibody against EDB-FN (ab154210, 1:500 for 2D, 1:100 for 3D; Abcam) in 1% (w/v) bovine serum albumin (BSA; Millipore, MA, USA)/0.1% (v/v) Triton X-100/PBS overnight at 4° C. After washing with PBS, immuno-labeled proteins were visualized by treatment with fluorescence-conjugated secondary antibodies at room temperature for 60 minutes. After washing with PBS, the cells were sealed with 4',6-diamidino-2-phenylindole (DAPI) mounting medium (Vector laboratories, CA, USA), and they were sealed with cover slips. Then, the examination was performed using a confocal laser scanning microscope (LSM 700; Carl Zeiss, NY, USA).

8.2. Paraffinized Tissue Microarrays and Immunohistochemistry of Animal Samples

The degree of EDB-FN staining was analyzed by applying tissue microarrays to patient tissue samples and immunohistochemistry to subcutaneous xenograft animal tissue samples. Tissue microarray slides were heated at 55° C. for 30 minutes to remove wax, washed three times for 5 minutes, and then washed with 100, 95, and 80% (v/v) ethanol for 5 minutes to continuously rehydrate to obtain pure distilled water. Antigen retrieval was performed by heating the section in 10 mM sodium citrate (pH 6.0) at 95° C. for 30 minutes. Endogenous peroxidase activity was inhibited by culture in 3% (w/v) hydrogen peroxide for 30 min. Background reactivity was removed using universal blocking serum (Dako Diagnostics) for 30 minutes at room temperature. The slides were treated with an EDB-FN-specific antibody (orb227981, 1:50; Biorbyt, Cambridge, UK) and cultured for 1 hour, and then they were treated with a biotin-labeled secondary antibody and cultured for 30 minutes. Streptavidin-peroxidase (Dako Diagnostics) was used and developed. After a slight counterstaining by treatment with hematoxylin, the slides were dehydrated and sealed with coverslips for microscopic observation.

<Example 9> Synthesis of Active Edb-Fn Target Micellar Nano-Dds 9.1 Synthesis of $APT_{EDB}$-conjugated $PEG_{2000}$-DSPE An additional cysteinylated EDB-FN-specific aptamer-like peptide ($APT_{EDB}$, Anygen) was dissolved in dimethyl sulfoxide (Sigma-Aldrich), and Mal-$PEG_{2000}$-DSPE was dissolved in chloroform (Sigma-Aldrich). A conjugation reaction was carried out for 12 hours at ambient temperature under inert conditions in a molar ratio of $APT_{EDB}$: Mal-$PEG_{2000}$-DSPE of 1:2. $APT_{EDB}$-conjugated $PEG_{2000}$-DSPE ($APT_{EDB}$-DSPE) was purified by reversed-phase high-performance liquid chromatography, and the conjugation efficiency was determined using matrix-assisted laser desorption/ionization time-of-flight mass spectrometry. In order to remove unconjugated peptides, dialysis was performed based on a molecular weight of 3.5 kDa using a dialysis membrane (Spectrum Chemical, NJ, USA). After 48 hours, the conjugates were lyophilized under reduced pressure.

9.2. Preparation of Micellar Nano-DDS Treated with $APT_{EDB}$-DSPE of Various Weight Percentages Anionic lipid film of 2 mg/mL of $PEG_{2000}$-DSPE was prepared from the stock solution. In order to prepare fluorescence-labeled micellar nano-DDS, Rh-DSPE labeled with 0.5 wt % rhodamine B fluorophore was added to $PEG_{2000}$-DSPE solution. $APT_{EDB}$-DSPE was added to the preparation at a concentration of 1.0, 2.5, or 5.0 wt %. For example, in order to form an active target $APT_{EDB}$-DSPE micellar nano-DDS of 1.0 wt % $APT_{EDB}$-DSPE ($APT_{EDB}$-conjugated), 20 µg of $APT_{EDB}$-DSPE conjugate was added to 2 mg/mL of $PEG_{2000}$-DSPE solution containing 0.5 wt % Rh-DSPE. Passive/nontargeting $PEG_{2000}$-DSPE micellar nano-DDS ($APT_{EDB}$-unconjugated) was synthesized as a negative control. All components were placed in a glass vial, dried under vacuum, and freeze-dried under reduced pressure overnight to remove all remaining chloroform. In order to obtain 2 mg/mL of final micelle solution, 1 mL of ultrapure water (Welgene) was added to the lipid film during rehydration. In order to form uniformly sized micelles, rehydration was performed under constant agitation of 1,000 revolutions per minute. The micellar solution was changed to PBS buffer using Amicon Ultra-15 centrifugal filter 3 kDa Units (Merck, Darmstadt, Germany). In order to remove over-sized nanoparticles or aggregates, the solution was filtered through a 0.1-µm membrane (Millipore) and purified by size exclusion chromatography (CL-4B column; Merck). After preparation, the size and zeta potential of all micellar preparations in PBS were analyzed by dynamic light scattering (DLS) and zeta potential analysis. 1 mL of 2 mg/mL micelles was transferred to a transparent cuvette, and the hydrodynamic diameter and zeta potential of each micelle were measured using a Zetasizer Nano ZS90 (Malvern Instruments, Malvern, UK).

9.3. Synthesis and Development of DSPE-DTX and $APT_{EDB}$-DSPE-DTX

Passive/nontargeting DSPE-DTX ($APT_{EDB}$-unconjugated) and active target $APT_{EDB}$-DSPE-DTX ($APT_{EDB}$-conjugated) were developed by applying the previously disclosed method (Chong K et al., Chem Commun (Camb). 2013; 49: 11476-8). First, to obtain $APT_{EDB}$-DSPE lipid, cysteinylated $APT_{EDB}$ was conjugated with the maleimide group of $PEG_{2000}$-DSPE lipid. In order to load DTX, DTX was dissolved in chloroform and added to the micellar lipid film to a final concentration of 50 mg/mL during rehydration. In the present invention, DTX-loaded $PEG_{2000}$-DSPE micellar nano-DDS and $APT_{EDB}$-DSPE micellar nano-DDS were named 'DSPE-DTX' and '$APT_{EDB}$-DSPE-DTX', respectively. DSPE-DTX and $APT_{EDB}$-DPSE-DTX were filtered through a 0.1-$\mu$m membrane and purified by size exclusion chromatography.

<Example 10> EDB-FN Validation as Therapeutic Target for Malignant Gliomas Using $APT_{EDB}$-Conjugated Micellar Nanoparticles 10.1. In Vitro Cellular Uptake of $APT_{EDB}$-DSPE Micellar Nano-DDS The cell uptake efficiency of $APT_{EDB}$-DSPE micellar nano-DDS was determined by treating EDB-FN-positive U87MG and U251MG cells with each micelle preparation. U87MG and U251MG cells were cultured in 96-well plates at 5,000 cells/well. After culturing the cells to confluence on sterile coverslips, the cells were treated with $APT_{EDB}$-DSPE at a concentration of 1.0, 2.5, or 5.0 wt % and were cultured with 100 $\mu$g/mL $PEG_{2000}$-DSPE micellar nano-DDS or $APT_{EDB}$-DSPE micellar nano-DDS at 37° C. for 1 hour. The cells were washed with PBS, fixed with 4% (w/v) paraformaldehyde, counterstained with nuclear dye DAPI (Invitrogen, CA, USA) and then encapsulated with glass slides. They were confirmed with a confocal laser scanning microscope in order to confirm the absorption rate of rhodamine B-labeled micelles.

10.2. Competition Assay

EDB-FN high-expressing cells (U87MG and U251MG) and EDB-FN low-expressing cells (MCF-7 and B16F1) were cultured on glass coverslips until they reached about 80% confluence. The cells were pretreated with free $APT_{EDB}$ peptide at various concentrations (100 $\mu$g/ml and 500 $\mu$g/ml) for 30 minutes. Then, rhodamine-labeled $APT_{EDB}$-DSPE was added, and the cells were cultured for an additional 30 minutes. Then, the cells were washed with PBS, fixed with 4% (w/v) paraformaldehyde, and sealed with a microscope slide for observation by a confocal microscope.

10.3. Transfection of siRNA (Small Interfering RNA)

EDB-FN-specific siRNA and scrambled control siRNA were purchased from Bioneer (Daejeon, Republic of Korea). The target sequence of EDB-FN siRNA used for RNA interference is as follows: sense; ACAGUCCCAGAU-CAUGGAG, antisense; CUCCAUGAUCUGGGACUGU. For transfection with Lipofectamine 2000 (Invitrogen, CA, USA), cells were grown overnight and then cultured in 96-well or 6-well plate at 60 to 70% confluence. Lipofectamine-siRNA complexes were prepared according to the manufacturer's instructions. Transfection efficacy was analyzed after 48 hours.

10.4. In vitro cellular Pptake of $APT_{EDB}$-DSPE Micellar nano-DDS

In order to confirm the intracellular uptake according to the expression level of EDB-FN, U87MG cells were transfected with the above-described control siRNA or EDB-FN siRNA. The transfected cells were treated with 100 $\mu$g/mL of $PEG_{2000}$-DSPE micellar nano-DDS or $APT_{EDB}$-DSPE micellar nano-DDS at a concentration of 1.0 wt % and cultured at 37° C. for 1 hour. $APT_{EDB}$-DSPE was stained by immunocytochemistry using an antibody against EDB-FN and encapsulated with DAPI-containing mounting solution. In order to confirm time-dependent cellular uptake, U87MG cells were treated with 100 $\mu$g/mL of $APT_{EDB}$-DSPE micellar nano-DDS with $APT_{EDB}$-DSPE at a concentration of 1.0 wt % for 5 minutes, 15 minutes, 30 minutes, 1 hour, and 4 hours.

10.5. In Vitro Cytotoxicity of $APT_{EDB}$-DSPE-DTX in U87MG and U251MG Cells

In order to determine the utility and value of EDB-FN as a molecular target for malignant gliomas, DTX was encapsulated into the core of $PEG_{2000}$-DSPE and $APT_{EDB}$-DSPE micellar nano-DDSs by the method described above. Each nano-DDS formulation was serially diluted and co-cultured with cells for 24 hours. After removing the preparation, the cells were further cultured for 24 hours before Alamar Blue assay (Bio-Rad, CA, USA). The $IC_{50}$ value of each formulation was determined by ProBit analysis.

10.6. In Vivo Uptake of $APT_{EDB}$-DSPE Micellar nano-DDS in Subcutaneous Xenograft Model In the in vivo xenograft model, to evaluate the uptake of $APT_{EDB}$-DPSE micellar nano-DDS, U87MG cells were injected into the right flank of BALB/c nude mice (n=3 mice per group) at $5 \times 10^6$ cells/mouse. After three weeks, tumor growth was measured. The tumor volume was 80 to 120 $mm^3$. Then, 200 $\mu$g of $PEG_{2000}$-DSPE micellar nano-DDS in PBS or $APT_{EDB}$-DSPE micellar nano-DDS in PBS was injected into each mouse, and at pre-specified times (15, 30, 60, and 120 minutes), tumor uptake of rhodamine B-labeled micelles was compared using an IVIS in vivo imaging system (PerkinElmer, MA, USA).

10.7. In Vivo Uptake and Toxicity of $APT_{EDB}$-DSPE

In order to evaluate in vivo tissue uptake of $APT_{EDB}$-DPSE micellar nano-DDS, U87MG cells were injected into the right flank of BALB/c nude mice at $5 \times 10^6$ cells/mouse (n=3 mice per group). After three weeks, tumor growth was measured. The tumor volume was determined to be 80 to 120 $mm^3$. Then, 200 $\mu$g of $PEG_{2000}$-DSPE micellar nano-DDS or $APT_{EDB}$-DSPE micellar nano-DDS was injected into each mouse, and at pre-specified times (6, 12, 24, and 48 hours), tumor uptake of rhodamine B-labeled micelles was compared using an IVIS in vivo imaging system (PerkinElmer, MA, USA).

In order to verify the safety of $APT_{EDB}$-DSPE, the weights of mice were checked before and after the experiment. At the end of the experiment, mice were euthanized to collect major organs (heart, lung, spleen, lung, and kidney) for H&E staining.

10.8. Immunohistochemistry of Frozen Samples of Subcutaneous Xenograft Model

The brain slice of the subcutaneous xenograft model attached to the slide glass was washed twice with cold PBS, blocked, and then permeated with a blocking buffer (PBS containing 0.3% Triton X-100 and 2% BSA) for 1 hour. A major antibody specific for EDB-FN (ab154210 Abcam, MA, USA) was diluted at 1:100 in blocking buffer and cultured with the tissue overnight at 4° C. After washing with PBS, they were treated with Alexa Fluor 488-conjugated secondary antibody (A11001; Invitrogen, CA, USA) diluted 1:200 in blocking buffer and cultured at room temperature for 1 hour. The tissues were counterstained with 4',6-diamidino-2-phenylindole (DAPI, Invitrogen, NY, USA), covered with cover slides, and then confocal laser scanning microscopy and slide scanner (Axio Scan.Z1; Carl Zeiss, NY, USA) were used for analysis.

10.9. In Vivo Anti-Cancer Efficacy of $APT_{EDB}$-DSPE-DTX

In order to construct a flank subcutaneous xenograft mouse model, U87MG cells were injected into the right flanks of BALB/c nude mice at $5 \times 10^6$ cells/mouse. When the tumor volume reached 80 to 120 $mm^3$, DPSE-DTX in PBS or $APT_{EDB}$-DSPE-DTX in PBS at a DTX concentration of 5 mg/kg in saline (including n=1 mouse per group for representative tumor tissue extraction, n=5 mice per group) was intravenously injected into mice. Based on the previous study protocol, each preparation was injected intravenously three times every two days. Tumor size was measured once every three days until excision. Tumor volume was calculated using the following formula: length×width×height× 0.5. Tumor inhibitory rate was calculated using the following formula: $[1-\{(T_{DayE}-T_{Day1})/T_{Day1}\times C_{Day1}/(C_{DayE}-C_{Day1})\}]\times100$ ($T_{DayE}$=final tumor volume in experimental group; $T_{Day1}$=first tumor volume (Day 1) in experimental group; $C_{DayE}$=final tumor volume in control group; $C_{Day1}$=initial tumor volume in control group).

In order to fabricate orthotopic xenograft mouse models, the heads of BALB/c nude mice were fixed with a stereotactic device, a small burr hole was made with a high-speed drill on 2 mm lateral from the bregma and 1 mm front surface from the coronal suture according to the method of Ozawa and James. U87MG cells were injected to a depth of 3 mm from the inner cortical bone of the skull at $3\times10^5$ cells/mouse using a 22-gauge needle (Hamilton Company, NV, USA). After seven days, mice were intravenously injected with saline once and DSPE-DTX or $APT_{EDB}$-DSPE-DTX at a concentration of 10 mg/kg DTX once (n=4 mice per group). On day 21 post-transplantation, mice were sacrificed for tumor size analysis. After spraying with 10% (v/v) formalin (Sigma-Aldrich), each brain was removed and inserted into an optimal cutting temperature compound (Sakura Finetek, Tokyo, Japan). The brain samples were frozen and sliced into 20 μm using cryostat sectioning. The brain slice was stained using a hematoxylin and eosin (H&E) staining kit (ScyTek, UT, USA), and the tumor volume was calculated using the following formula: (length×width×width)×0.5. The longest dimension was set as the length, and the longest vertical diameter was set as the width.

<Example 11> Imaging and Statistical Analysis

Image processing and data analysis were performed using ImageJ software (http://rsb.info.nih.gov/ij/). All data were analyzed using GraphPad Prism 7 software (GraphPad, La Jolla, CA, USA), and were indicated as means±standard deviations (std. devs.) except for $IC_{50}$ values expressed as means±standard errors (std. errors). For comparison between groups, the unpaired two-tailed t test with Welch's correction (Welch's t test) was mainly performed for normally distributed data, and the Mann-Whitney test was performed for non-normally distributed data. P values of <0.05 were considered to be statistically significant and were expressed as follows: p<0.05 (*), p<0.01 (), p<0.001 (*), and p<0.0001 (****).

<Example 12> Ethical Approval

All applicable international, national, and/or institutional guidelines were followed for animal testing. In the present invention, all experiments on animals met the ethical standards of KAIST Institutional Animal Care and Use Committee and Korea University College of Medicine (IACUC No. KA2013-13 and KOREA-2019-0123). The patient sample study complied with guidelines and protocols approved by the Korea University Guro Hospital Institutional Review Board (IRB No. 2017GR0330).

Experiment Result

The present inventor analyzed normalized big data and EDB-FN expression levels of patient tissue samples to evaluate whether EDB-FN is feasible as a marker and target for various cancers. In addition, the present inventor verified the usefulness of EDB-FN as a diagnostic marker and drug delivery target for malignant glioma as one of the cancers with the highest expression rate of EDB-FN in cancer cells compared to normal cells.

<Experimental Results 1> EDB-FN Expression in Cancer Cell Lines

The screening was performed to determine the level of EDB-FN expression in various human cancer cell lines. Breast cancer cell lines MCF7, prostate cancer cell lines PC3, melanoma cell lines B16F1 and B16F10, and malignant glioma cell lines U373MG, U87MG, and U251MG were used in the experiments. The expression pattern of EDB-FN protein was confirmed by quantitative analysis during two-dimensional monolayer culture (FIG. 1A). Weak EDB-FN expression was detected in the PC3 cell line and U373MG cell line, but the clear expression was observed in the U87MG cell line. In addition, qRT-PCR was performed by extracting mRNA for quantitative analysis of EDB-FN expression (FIG. 1B). As a result (MCF7, 47.8±7.9; PC3, 12.1±2.1; B16F1, 0.6±0.5; B16F10, 23.3±1.4; U373MG, 2.6±0.8; U251MG, 643.0±31.0; U87MG, 1430.3±61.4), a statistically significant overexpression was observed in the U251MG cell line (p<0.001, compared to all other cell lines, Welch's t test), and the highest expression was observed in the U87MG cell line (p<0.001, compared to all other cell lines, Welch's t test). From the above results, it was confirmed that EDB-FN was overexpressed in malignant gliomas compared to other cancers.

In order to create a tumor microenvironment, a malignant glioma cell line was cultured in 3D, and an animal model of a malignant glioma flank xenograft was prepared. As a result of quantitative analysis of EDB-FN expression using immunostaining, EDB-FN was more overexpressed in U87MG cell lines than in U251MG and U373MG cell lines during 3D culture (FIG. 1C). In the xenograft mouse model, U251MG and U87MG cell lines showed relatively higher expression patterns than U373MG cell lines (FIG. 1D). As a result of quantitative analysis through mRNA qRT-PCR (FIG. 1E), EDB-FN was significantly expressed in the U87MG cell line compared to the 2D cultured U373MG cell line (p<0.01, Welch's t test). Compared with the above results, the 3D cultured U87MG cell line mimicking the tumor microenvironment showed higher EDB-FN expression (p<0.001, compared to the 2D cultured U87MG cell line, Welch's t test), and the highest EDB-FN expression was exhibited in the xenograft animal model (p<0.0001, compared to the 3D cultured U87MG cell line, Welch's t test). These results suggest a linear correlation between EDB-FN expression and tumor microenvironment similarity in malignant gliomas, indicating that EDB-FN can be used as a biomarker for malignant gliomas.

Finally, EDB-FN was more overexpressed in malignant glioma cells than other cancer cells, and EDB-FN expression was relatively low in U373MG cells, which proliferate slowly among malignant glioma cell lines. The U87MG cell line, known to proliferate actively, showed the highest EDB-FN expression level, and the U251MG cell line with glioblastoma multiform stem cell-like characteristics showed the next level. Based on the above results, the U87MG and U251MG cell lines were used in the following study.

<Experimental Result 2> Characteristic Analysis of Synthetic $APT_{EDB}$-DSPE Micellar Nano-DDS As a result of dynamic light scattering (DLS) analysis of micelles, the $PEG_{2000}$-DSPE micellar nano-DDS showed a diameter of 11.5±1.9 nm, and $APT_{EDB}$-DSPE micellar nano-DDS treated with $APT_{EDB}$-DSPE at a concentration of 1.0, 2.5, and 5.0 wt % showed diameters of 8.2±1.3 nm, 10.5±1.9 nm, and 10.3±1.3 nm, respectively (FIGS. 2A and 2B). The decrease in the DLS-measured size of $APT_{EDB}$-DSPE micellar nano-DDS compared to $PEG_{2000}$-DSPE micellar nano-DDS and the increase in the measured size of $APT_{EDB}$-DSPE micellar nano-DDS in $APT_{EDB}$-DSPE at a concentration of 2.5 and 5.0 wt % compared to the same DDS at a concentration of 1.0 wt % indicated that the presence of $APT_{EDB}$ on the outer surface of micelles affected the morphological changes in micellar nano-DDS. The zeta potential of each nano-DDS (the surface charge of nanoparticles can be inferred) was measured: the zeta potential of $PEG_{2000}$-DSPE micellar nano-DDS was $-9.3\pm1.1$ mV, and the zeta potentials of $APT_{EDB}$-DSPE micellar nano-DDS treated with $APT_{EDB}$-DSPE at concentrations of 1.0, 2.5, and 5.0 wt % were $-9.5\pm0.7$ mV, $-10.4\pm1.3$ mV, and $-12.1\pm0.7$ mV, respectively (FIG. 2C).

<Experimental Result 3> Cell Uptake According to $APT_{EDB}$-DSPE Density

Figures 4A, 4B, 4C:
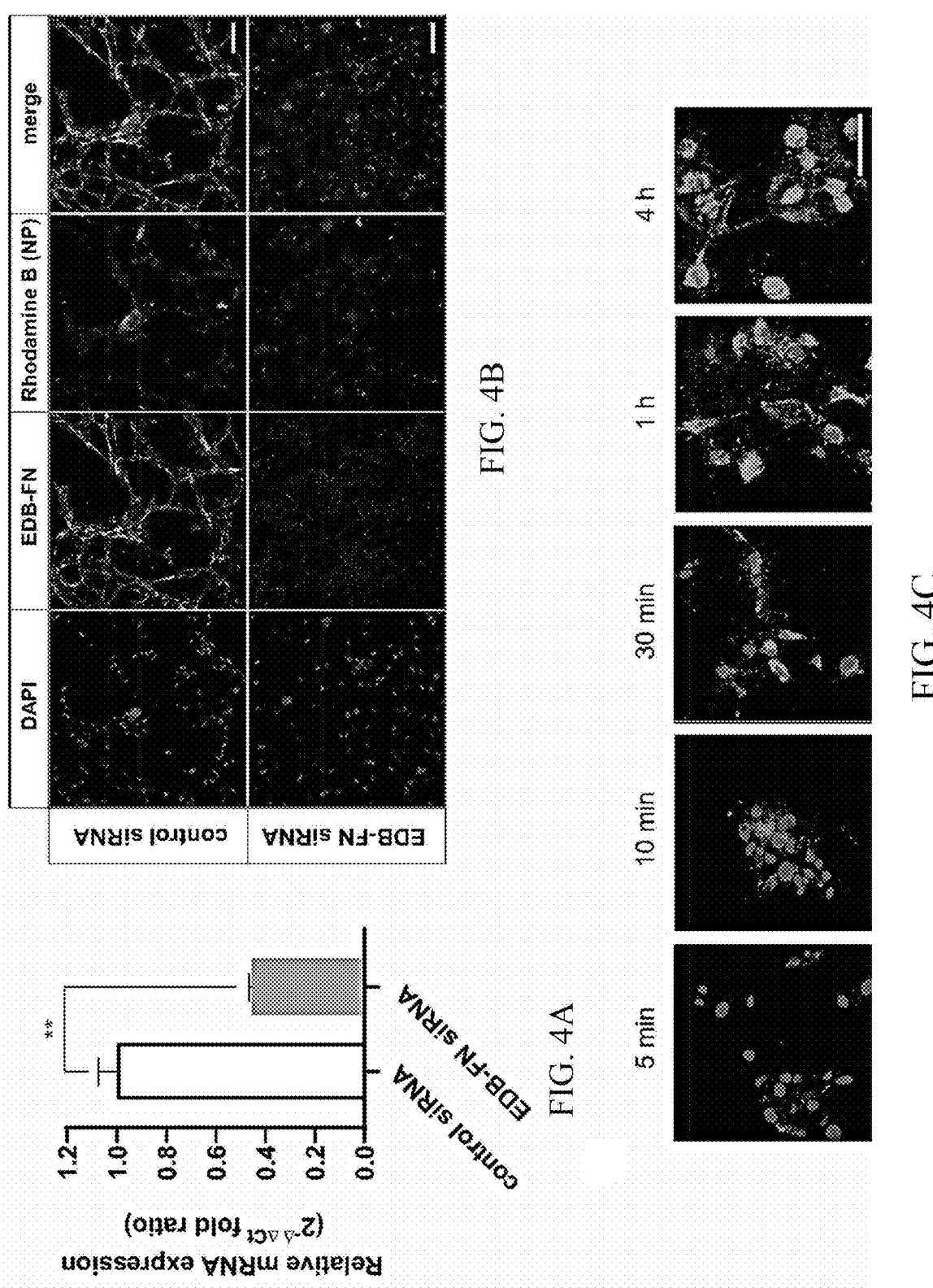
FIG. 4A confirms the siRNA-mediated EDB-FN knockdown through qRT-PCR. GAPDH expression was used as an internal control. Statistical analysis: Welch's t test. **p<0.01. The results are expressed as mean±standard deviation of triplicate determinations.
FIG. 4B shows the cellular uptake of $APT_{EDB}$-DSPE micellar nano-DDS according to EDB-FN expression. Staining images show EDB-FN (green), rhodamine B-labeled $APT_{EDB}$-DSPE micellar nano-DDS (red), and nuclei (blue) in siRNA-transfected U87 cells (size bar=100 μm).
FIG. 4C shows time-dependent cellular uptake of $APT_{EDB}$-DSPE micellar nano-DDS in U87MG cells. Red: Rhodamine B-labeled $APT_{EDB}$-DSPE micellar nano-DDS, blue: DAPI, size bar=100 μm. NP: nanoparticles.

In order to determine the optimized target ligand density, $APT_{EDB}$-DSPE was added to a chloroform solution of Rh-DSPE mixed with $PEG_{2000}$-DSPE at concentrations of 1.0, 2.5, and 5.0 wt % before lipid film formation. Under all conditions, the uptake efficacy of the active target $APT_{EDB}$-DSPE micellar nano-DDS in cancer cells was higher than that of the passive/nontargeting $PEG_{2000}$-DSPE micellar nano-DDS (FIG. 4A). Interestingly, $APT_{EDB}$-DSPE micellar nano-DDS treated with $APT_{EDB}$-DSPE at a concentration of 2.5 wt % showed the highest cellular uptake in U251MG cells ($PEG_{2000}$-DSPE, 44.5±9.6; 1.0% $APT_{EDB}$-DSPE, 76.4±8.1; 2.5% $APT_{EDB}$-DSPE, 128.8±12.1; 5.0% $APT_{EDB}$-DSPE, 53.4±5.1). Meanwhile, $APT_{EDB}$-DSPE micellar nano-DDS treated with $APT_{EDB}$-DSPE at a concentration of 1.0 wt % showed the highest cellular uptake in U87MG cells ($PEG_{2000}$-DSPE, 6.8±5.1; 1.0% $APT_{EDB}$-DSPE, 165.7±3.7; 2.5% $APT_{EDB}$-DSPE, 93.2±6.7; 5.0% $APT_{EDB}$-DSPE, 56.7±7.9). As the concentration of $APT_{EBD}$-DSPE increased, it became more negative (FIG. 2C). The decreased cellular uptake of $APT_{EDB}$-DSPE micellar nano-DDS treated with $APT_{EDB}$-DSPE at 5.0 wt % concentration may be partially explained through negative charge in nano-DDS. However, although both U87MG and U251MG cells were malignant glioma cells and the same target ligand was used, the concentration of $APT_{EDB}$-DSPE with the highest cellular uptake efficacy was different for each cell line. Therefore, it can be seen that the ligand density varies depending on the cell line and cell type, and thus the cellular uptake is also different.

Figures 3A, 3B:
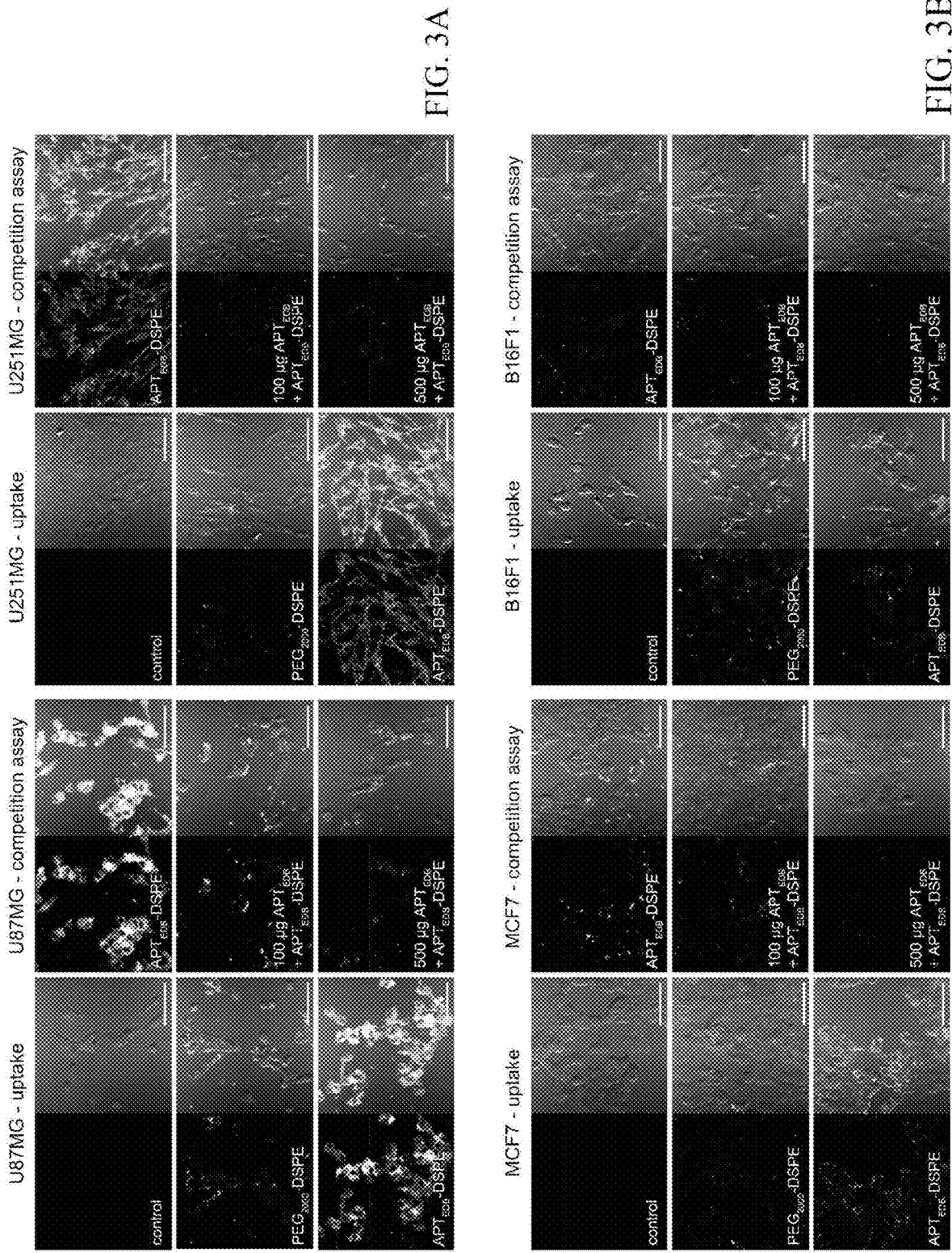
FIG. 3 shows the in vitro cell uptake of $APT_{EDB}$-DSPE micellar nano-DDS by EDB-FN expression. Uptake experiments and competition assay of PEG$_{2000}$-DSPE and $APT_{EDB}$-DSPE were performed in FIG. 3A EDB-FN high-expressing cells (U87MG and U251) and FIG. 3B low-expressing cells (MCF7 and B16F1). Phosphate buffered saline was compared as a control. PEG$_{2000}$-DSPE and $APT_{EDB}$-DSPE were added to cell lines with or without $APT_{EDB}$ treatment, and uptake (red) of rhodamine B-labeled micellar DDS was confirmed by confocal microscopy (size bar=100 μm). $APT_{EDB}$: EDB-FN-specific aptamer-like peptide (aptide); $APT_{EDB}$-DSPE: $APT_{EDB}$-conjugated PEG$_{2000}$-DSPE; PEG$_{2000}$-DSPE: polyethylene glycol (2000)-1,2-distearoyl-sn-glycero phosphoethanolamine.

In order to demonstrate the targeting ability of $APT_{EDB}$-DSPE micellar nano-DDS to EDB-FN, a competition analysis was performed by simultaneously treating high and low EDB-FN-expressing cells with an EDB-FN-targeting aptide and $APT_{EDB}$-DSPE micellar nano-DDS. The uptake of $APT_{EDB}$-DSPE micellar nano-DDS in U87MG and U251MG, high EDB-FN-expressing cells, decreased as the concentration of EDB-FN-targeting aptide increased. Although the uptake of $APT_{EDB}$-DSPE was minimal, EDB-FN-interfering effects were also observed in MCF-7 and B16F1, EDB-FN-low-expressing cells (FIGS. 3A and 3B).

To determine whether the active target $APT_{EDB}$-DSPE micellar nano-DDS was dependent on EDB-FN expression, EDB-FN was knocked down in U87MG cells. EDB-FN expression in U87MG cells was significantly reduced after EDB-FN-siRNA treatment; on the other hand, EDB-FN expression in cells treated with control siRNA (control siRNA, 1.00±0.08; EDB-FN siRNA, 0.45±0.01; p<0.01, Welch's t test) was constant (FIG. 4A). After treatment with the siRNA, there was no change in the uptake of the remaining amount of $APT_{EDB}$-DSPE micellar nano-DDS. However, in the cells in which EDB-FN expression was inhibited, the uptake of the active target $APT_{EDB}$-DSPE micellar nano-DDS was decreased (FIG. 4B). Moreover, time-dependent uptake of $APT_{EDB}$-DSPE micellar nano-DDS in U87 cells was also observed for 4 hours. After 5 minutes of treatment, $APT_{EDB}$-DSPE micellar nano-DDS concentration was gradually increased in cells, reaching saturation within 1 to 4 hours (FIG. 4C).

The above results suggest that $APT_{EDB}$-DSPE micellar nano-DDS is taken up by cells in an EDB-FN expression-dependent and time-dependent manner, indicating that, more clearly the target ligand density is important for cellular uptake of nanoparticles.

Figures 5A, 5B, 5C:
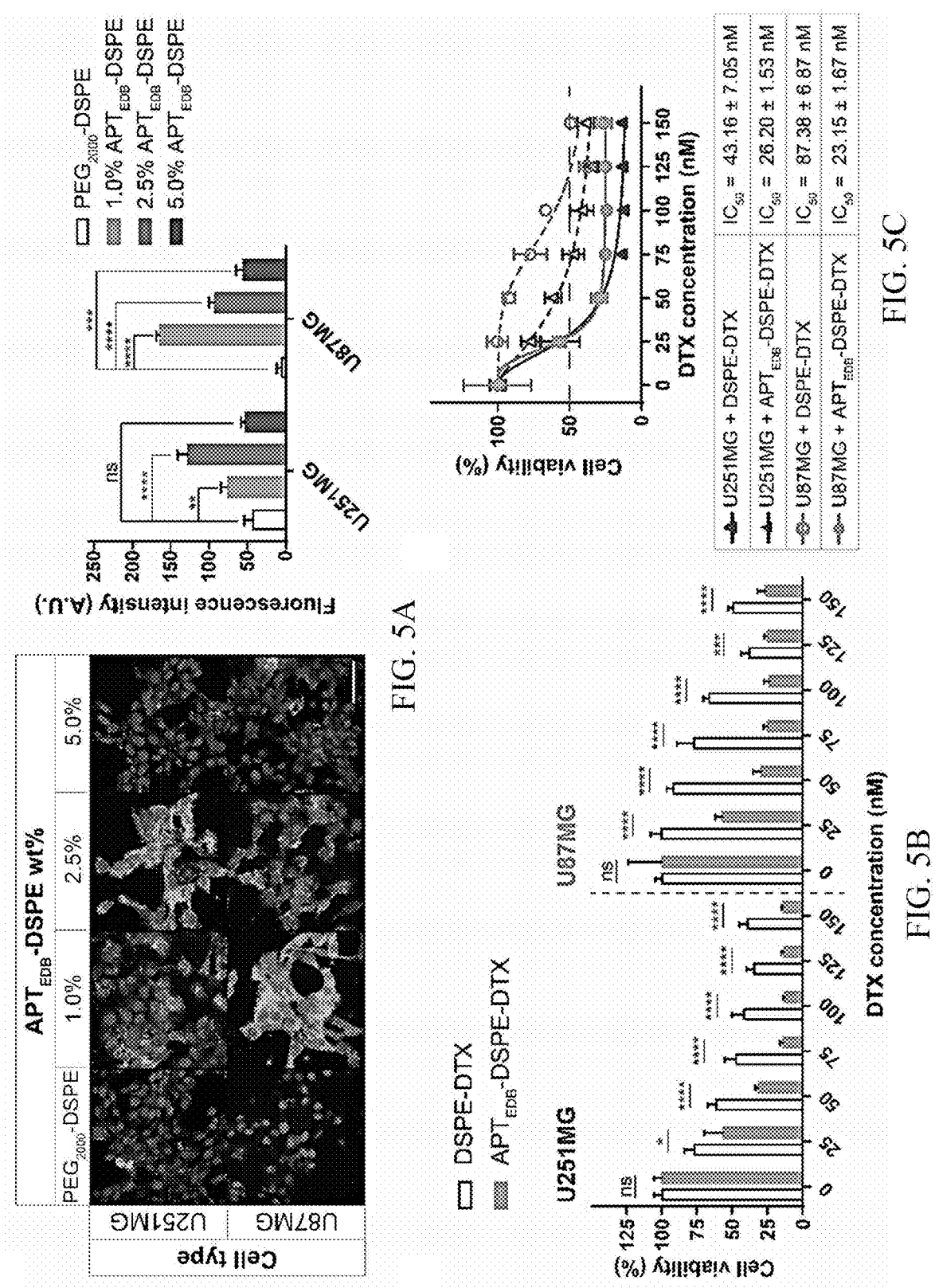
FIG. 5A shows the cellular uptake of rhodamine B fluorophore-labeled nano-DDSs according to the concentration of $APT_{EDB}$-DSPE in malignant glioma (left). Red: nano-DDSs, blue: DAPI, size bar=100 μm. Quantification analysis of $APT_{EDB}$-DSPE micellar nano-DDS cellular uptake is shown via ImageJ (right). Fluorescence intensity was normalized to the DAPI signal of each cell line (quadruplet determinations).
FIG. 5B shows the in vitro cytotoxicity of DSPE-DTX and $APT_{EDB}$-DSPE-DTX in U251MG and U87MG cells. O.D. value obtained by Nano-DDS treatment were divided by O.D. values obtained by PBS treatment (7 replicates for DSPE-DTX, 6 replicates for $APT_{EDB}$-DSPE-DTX) to calculate % cell viability on the y-axis.
FIG. 5C shows the $IC_{50}$ values in U87MG and U251MG cells calculated according to the type of nanoparticles used for treatment (7 replicates for DSPE-DTX, 6 replicates for $APT_{EDB}$-DSPE-DTX). Statistical analysis: Welch's t test. *p<0.05, p<0.01, *p<0.001, ****p<0.0001, ns: not statistically significant. The results are expressed as mean±standard deviation. A.U: arbitrary unit. $APT_{EDB}$-DSPE: $APT_{EDB}$-conjugated PEG$_{2000}$-DSPE; $APT_{EDB}$-DSPE-DTX: DTX-loaded $APT_{EDB}$-DSPE micellar nano-DDS; DSPE-DTX: DTX-loaded PEG$_{2000}$-DSPE micellar nano-DDS; DTX: docetaxel; PEG$_{2000}$-DSPE: polyethylene glycol (2000)-DSPE (ammonium salt).

<Experimental Result 4> Improvement of Cancer Target and Anti-Cancer Efficacy by Targeting EDB-FN 4.1. In Vitro Toxicity of $APT_{EDB}$-DSPE-DTX In order to determine the value and utility of EDB-FN as a molecular target for malignant gliomas, DTX was encapsulated into the core of $PEG_{2000}$-DSPE and $APT_{EDB}$-DSPE micellar nano-DDS. The loading capacity of each micellar nano-DDS was calculated as 10 wt %, and the encapsulation efficiency was calculated as about 95%. Cell viability was assessed using DSPE-DTX and $APT_{EDB}$-DSPE-DTX (FIG. 5B). DTX inhibited the viability of U251MG and U87MG cells in the DSPE-DTX and $APT_{EDB}$-DSPE-DTX systems, but the degree of inhibition was different. $IC_{50}$ values in U87MG cells were 87.38±6.87 nM for DSPE-DTX and 23.15±1.67 nM for $APT_{EDB}$-DSPE-DTX, and $APT_{EDB}$-DSPE-DTX was about 3.8 times lower than DSPE-DTX (p<0.0001, Welch's t test). $IC_{50}$ values in U251MG cells were 43.16±7.05 nM for DSPE-DTX 26.20±1.53 nM for $APT_{EDB}$-DSPE-DTX, and $APT_{EDB}$-DSPE-DTX was about 1.6 times lower than DSPE-DTX (p<0.05, Welch's t test) (FIG. 5C). In vitro cytotoxicity data in U87MG and U251MG cells suggest superior cancer-targeting ability, and it is thought that an increase in drug uptake could be achieved through EDB-FN active targeting compared to passive/nontargeting. As a significant difference between the $IC_{50}$ values of DSPE-DTX and $APT_{EDB}$-DSPE-DTX was observed in U87MG cells, U87MG cells were selected for use in in vivo modeling and evaluation of EDB-FN as a molecular target for malignant gliomas.

4.2. In Vivo Uptake of $APT_{EDB}$-DSPE Micellar Nano-DDS

Figures 7A, 7B, 7C:
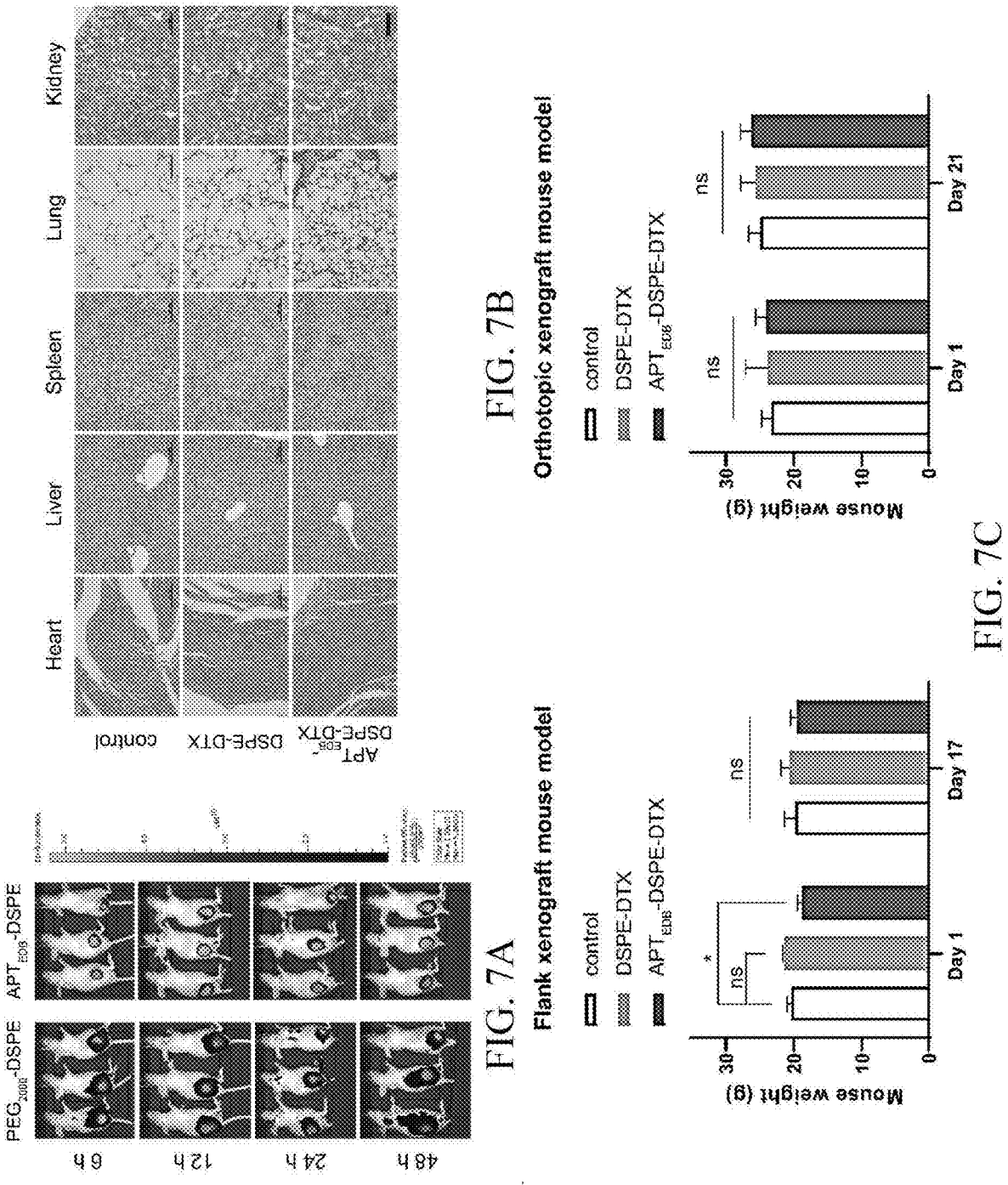
FIG. 7A shows the cancer-targeting ability of $APT_{EDB}$-DSPE-DTX. Each U87MG flank xenograft mouse (n=3 mice per group) was injected with PEG$_{2000}$-DSPE micellar nano-DDS or $APT_{EDB}$-DSPE micellar nano-DDS, and at pre-specified times (6, 12, 24, and 48 hours), tumor uptake of rhodamine B-labeled micelles was compared using the IVIS in vivo imaging system. Size bar=1 cm. FIG.
FIG. 7C shows the minimal toxicity of micellar nano-DDS on mouse body weight in the U87MG subcutaneous xenograft model (left, n=3 mice per group). In the experiment, the body weights of the mice were measured daily, and the initial and final body weights of the mice were graphed. Statistical analysis: Welch's t test. *p<0.05. The results are expressed as mean±standard deviation. APT$_{EDB}$-DSPE-DTX: docetaxel-loaded APT$_{EDB}$-DSPE micellar nano-DDS; DSPE-DTX: docetaxel-loaded PEG$_{2000}$-DSPE micellar nano-DDS.

A real-time IVIS imaging study in the U87MG flank xenograft mouse model indicated that $APT_{EDB}$-DSPE micellar nano-DDS showed a significant increase in tumor localization compared to passive/nontargeting $PEG_{2000}$-DSPE micellar nano-DDS: The increase in tumor localization was continuously observed from 15 minutes to 120 minutes (FIG. 6A). At 15 minutes, minimal nanoparticle accumulation was observed. After 30 minutes, higher accumulation started in the $APT_{EDB}$-DSPE micellar nano-DDS group. After 60 minutes, the $APT_{EDB}$-DSPE micellar nano-DDS group showed more accumulation at the tumor site than the $PEG_{2000}$-DSPE micellar nano-DDS group. In addition, to determine whether DDS affects organs other than tumors, tissue uptake of micellar nano-DDS was measured for 48 hours (FIG. 7A). Passive/nontargeting $PEG_{2000}$-DSPE micellar nano-DDS was gradually diffused throughout the body within 48 hours. However, $APT_{EDB}$-DSPE micellar nano-DDS remained stable, limited tumor sites. These results indicate the stability and high malignant glioma-targeting ability of $APT_{EDB}$-DSPE micellar nano-DDS. As $APT_{EDB}$-DSPE has a high EDB-FN targeting ability, it binds to EDB-FN with high affinity, showing a significantly increased retention time of $APT_{EDB}$-DSPE micellar nano-DDS in malignant gliomas. Thus, it had the bioavailability of the drug in increased tumors.

4.3. In Vivo Anti-Cancer Efficacy of $APT_{EDB}$-DSPE-DTX

The in vivo anti-cancer efficacy was verified in the U87MG subcutaneous xenograft animal model. The efficacy was assessed by comparing the trends in tumor growth in control, DSPE-DTX, and $APT_{EDB}$-DSPE-DTX groups over time (FIG. 6B). In the control group, the tumor volume increased about 5.9-fold within the 16th day (day 17) compared to the first day (day 1) (Day 1: 91.5±7.4 $mm^3$ vs. Day 17: 538.0±115.9 $mm^3$; p<0.01, Welch's t test). Tumor growth was significantly inhibited by treatment with DSPE-DTX or $APT_{EDB}$-DSPE-DTX. As a result of calculating the percentage of tumor inhibition as described above, it was confirmed that DSPE-DTX inhibited tumor growth by about 54.8% (Day 1: 87.9±12.6 $mm^3$ vs. Day 17: 281.7±29.4 $mm^3$;

p<0.001, Welch's t test), whereas $APT_{EDB}$-DSPE-DTX significantly inhibited tumor growth by about 97.6% (Day 1: 87.5±12.6 mm³ vs. Day 17: 97.8±2.6 mm³; p<0.20, Welch's t test). On the first day, tumor volume did not differ significantly between groups. However, on days 2, 4, and 6 of three doses of nano-DDS, the difference in tumor volume between groups became significant over time (FIGS. 6C and 6D). The $APT_{EDB}$-DSPE-DTX group showed significant tumor inhibition from day 7 compared to the control group (p<0.001, Welch's t test), and there was a difference from day 17 when compared with the DSPE-DTX group (p<0.01, Welch's t test).

As shown in FIG. 7B, as a result of administering the micellar nano-DDS into the body, no side effects were observed in major organs such as heart, liver, spleen, lung, and kidney, and there was no significant change in the weights of the mice until the end of the experiment (Day 1, control=20.4±0.6 g, DSPE-DTX=21.4±0.2 g, $APT_{EDB}$-DSPE-DTX=18.9±0.6 g; Day 17, control=19.8±1.6 g, DSPE-DTX=20.7±1.2 g, $APT_{EDB}$-DSPE-DTX=19.5±0.9 g) (FIG. 7C). This indicates that $APT_{EDB}$-DSPE micellar nano-DDS has almost no toxicity and thus has biocompatibility.

Figure 8B:
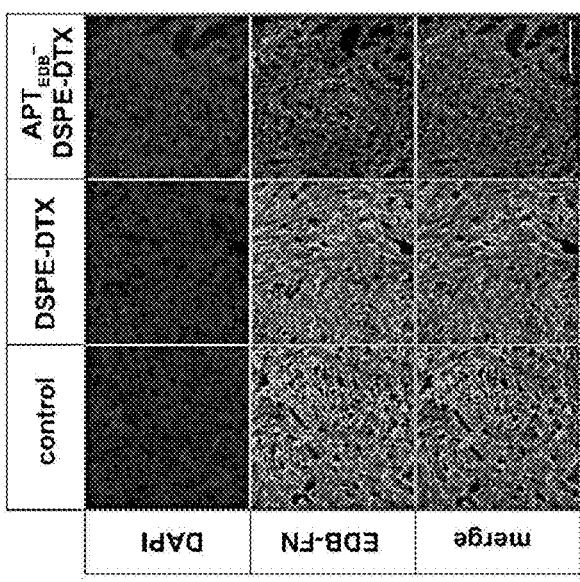
FIG. 8B shows an enlarged image of the tumor site. Size bar=100 μm. APT$_{EDB}$-DSPE-DTX: docetaxel-loaded APT$_{EDB}$-DSPE micellar nano-DDS; DSPE-DTX: docetaxel-loaded PEG$_{2000}$-DSPE micellar nano-DDS.

4.4. Anti-Cancer Efficacy of $APT_{EDB}$-DSPE-DTX in Orthotopic Brain Tumor Mouse Model In order to evaluate its feasibility as a therapeutic target for brain tumors, the U87MG orthotopic xenograft animal model was constructed. As shown in FIG. 6E, saline was set as a control group, and DSPE-DTX and $APT_{EDB}$-DSPE-DTX were injected intravenously for 7 days after cell transplantation (n=4 mice per group). After 2 weeks, the brains were extracted, and the tumor volumes of each group were compared. Normal and tumor localizations of sliced brain tissue were performed using H&E staining, and the size of the tumor was measured based on the slice of the largest tumor in each model (FIGS. 6F and 6G). As a result, it was found that tumor growth was significantly inhibited by EDB-FN-targeting micellar nano-DDS treatment. The DSPE-DTX (86.7±28.7 mm³) and $APT_{EDB}$-DSPE-DTX (46.5±27.0 mm³) groups inhibited tumor growth by 25.8% (p<0.15, Welch's t test) and 60.2% (p<0.01, Welch's t test), respectively, compared with the control group (116.9±21.0 mm³). Although there was no statistically significant difference, the $APT_{EDB}$-DSPE-DTX group showed approximately 34.4% higher tumor growth inhibition than the DSPE-DTX group (p<0.09, Welch's t test). No significant body weight changes were observed in all groups during the experiment (Day 1, control=22.7±1.3 g, DSPE-DTX=23.3±2.5 g, $APT_{EDB}$-DSPE-DTX=23.3±1.6 g; Day 21, control=24.5±1.3 g, DSPE-DTX=25.1±1.7 g, $APT_{EDB}$-DSPE-DTX=25.5±1.5 g) (FIG. 8C). The above results indicate that the EDB-FN-targeting micellar nano-DDS of the present invention has the potential to treat malignant gliomas, and that EDB-FN is a useful target for drug treatment.

Figure 8A:
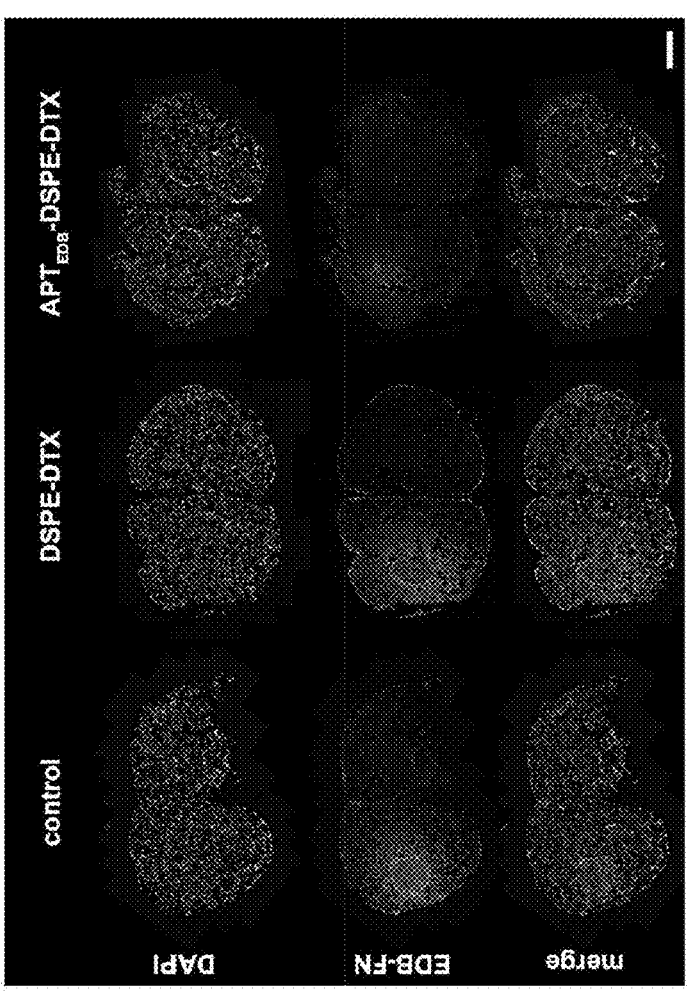
FIG. 8A shows IHC images with EDB-FN (green) and Nuclei (blue). Size bar=1 mm.

In order to confirm that transplanted U87MG cells overexpress EDB-FN in an orthotopic mouse model of malignant glioma, immunohistochemical analysis was performed using mouse brain slices containing tumors in all groups. Compared with normal regions of mouse brain tissue, EDB-FN was expressed higher in tumor regions of all groups (FIG. 8A). Interestingly, EDB-FN expression in the tumor was slightly decreased in the $APT_{EDB}$-DSPE-DTX group compared with the control and DSPE-DTX groups (FIG. 8B), indicating that there is a possibility that $APT_{EDB}$-DSPE-DTX affected the EDB-FN expression level in the tumor.

<Review>

The present invention relates to EDB-FNs located on the surface and within the extracellular matrix of cancer cells. More specifically, the protein on the surface and in the extracellular matrix can be utilized as a useful target for drug delivery systems (DDSs), as well as a cancer diagnostic biomarker.

Considering the above results, the present inventors performed in vitro and in vivo experiments including subcutaneous xenograft animal model experiments for verification. BBTB in which BBB developed to prevent bacteria from invading the central nervous system was applied, has a microphysiological pore size smaller than 12 nm, so the use of nano-DDS with a much smaller size can ensure easy permeation through the BBTB. Therefore, to improve drug delivery, the present inventors used DSPE polymer to develop ultra-small micelles (~12 nm) and attached $APT_{EDB}$ to the surface of micelles to construct a system that can be used for diagnosis and treatment of malignant glioma. Conventionally, the drug delivery system was very large, including liposomes with a size of about 115±13 nm or superparamagnetic iron oxide nanoparticles with a size of 34 nm, but the present invention has greatly reduced it to small micelles with 12 nm (FIG. 2).

Figure 9:
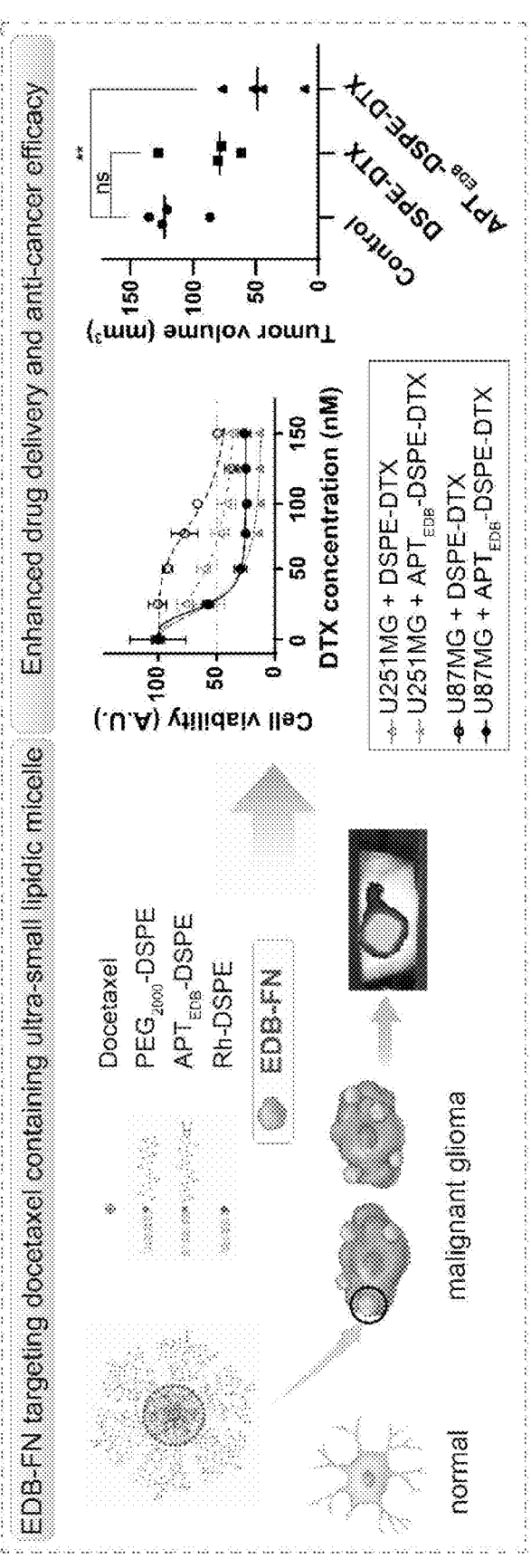
FIG. 9 shows the clinical significance of EDB-FN as a potential biomarker and its feasibility as a target ligand for malignant gliomas.

The present inventors quantitatively compared the correlation between the EDB-FN expression level and the patient's prognosis (FIG. 2) and verified the usefulness of the EDB-FN target in malignant gliomas (FIGS. 5 and 6). The enhanced drug delivery by EDB-FN overexpression and EDB-FN-targeting DDS were confirmed in monolayer cell culture as well as in orthotopic xenograft models, indicating that EDB-FN is expressed in malignant glioma cells and tissues, and nano-DDS is linked to or based on malignant gliomas through EDB-FN targeting (FIG. 9). Although the DTX dose for the orthotopic xenograft animal model was determined to be a total of 10 mg/kg, which was 33% less than 15 mg/kg for the flank xenograft animal model, the xenograft model showed significant anti-cancer efficacy as seen in the flank model. Despite the limitations of BBTB, the prepared EDB-FN-targeting micellar nano-DDS showed a significant therapeutic effect compared to the nontargeting micellar nano-DDS without statistically significant anti-cancer efficacy. The specific binding of $APT_{EDB}$ to malignant glioma cells effectively increased the tumor retention time of $APT_{EDB}$-DSPE micellar nano-DDS, demonstrating excellent anti-cancer efficacy. EDB-FN showed high expression specifically in malignant glioma tissues but the minimal expression in adjacent normal tissues and normal brain tissues. These properties will help to increase the feasibility of using EDB-FN as a target ligand for the treatment of malignant gliomas.

As described above in detail a specific part of the content of the present invention, it is clear for those of ordinary skill in the art that this specific description is only a preferred example embodiment, and the scope of the present invention is not limited thereto. Accordingly, the substantial scope of the present invention is defined by the appended claims and their equivalents.

INDUSTRIAL APPLICABILITY

The present invention relates to a micelle-structured drug delivery system including a $PEG_{2000}$-DSPE polymerized lipid and an $APT_{EDB}$-$PEG_{2000}$-DSPE polymer, and the drug delivery system targets extradomain B of fibronectin (EDB-FN), which is overexpressed in brain tumors and passes through the blood-brain barrier (BBB) or the blood-brain tumor barrier (BBTB) so that it delivers drugs specifically to brain tumor cells. Therefore, the composition including the drug delivery system of the present invention loaded with a drug such as a contrast agent or an anti-cancer agent as an active ingredient may be accumulated inside the brain tumor and be incorporated into the tumor cells so that it may be useful in the field of brain tumor diagnosis and treatment.

What is claimed is:

1. A method of producing a brain tumor-specific drug delivery system, the method comprising steps of:

(1) mixing $APT_{EDB}$ containing cysteine residues and Mal-PEG$_{2000}$-DSPE in an organic solvent in a molar ratio of 1:2 and inducing polymerization;

(2) obtaining an $APT_{EDB}$-PEG$_{2000}$-DSPE polymer from the mixed solution of step (1);

(3) mixing the $APT_{EDB}$-PEG$_{2000}$-DSPE polymer and PEG$_{2000}$-DSPE polymerized lipid in one or more solvents selected from the group consisting of water, PBS, HBS, and HBG to induce formation of a micelle structure; and (4) filtering the mixed solution of step (3) and purifying the micellar structure to yield micelles having a hydrodynamic diameter of 7-12 nm and a zeta potential of −8.2 to −12.8 mV as measured by dynamic light scattering, wherein the $APT_{EDB}$ of step (1) is an aptide that exhibits specific binding ability to extradomain B of fibronectin (EDB-FN) gene (Entrez Gene ID: 2335).

2. The method of claim 1, wherein the organic solvent of step (1) includes at least one selected from the group consisting of chloroform, dimethyl sulfoxide, dimethylformamide, ethanol, methanol, tetrahydrofuran, toluene, xylene, and hexane.

3. The method of claim 1, wherein the step (1) is performed under inactive conditions for 12 hours at room temperature.

4. The method of claim 1, wherein the step (2) is performed to obtain the $APT_{EDB}$-PEG$_{2000}$-DSPE polymer from the mixed solution using liquid chromatography.

5. The method of claim 1, wherein the step (3) is performed in which the $APT_{EDB}$-PEG$_{2000}$-DSPE polymer and PEG$_{2000}$-DSPE polymerized lipid are mixed in a solvent and sonicated to hydrate, thereby inducing the formation of the micelle structure.

6. The method of claim 1, wherein the step (4) is performed in which the mixed solution is filtered with a 0.025 to 0.1 μm membrane, and the micelle structure is purified through size exclusion chromatography.

7. A method of producing a drug for treating brain tumors, the method comprising steps (1) to (4) of claim 1, wherein the step (3) is performed in which an anti-cancer agent is additionally mixed in a solution in which $APT_{EDB}$-PEG$_{2000}$-DSPE polymer and PEG$_{2000}$-DSPE polymerized lipid are dissolved, thereby inducing formation of a micelle structure.

8. The method of claim 7, wherein the anti-cancer agent is mixed so that a final concentration is 50 mg/mL.

* * * * *